United States Patent
De Villartay et al.

(10) Patent No.: US 7,534,874 B2
(45) Date of Patent: May 19, 2009

(54) GENE INVOLVED IN V(D)J RECOMBINATION AND/OR DNA REPAIR

(75) Inventors: Jean-Pierre De Villartay, Yerres (FR); Despina Moshous, Castrop-Rauxel (DE); Alain Fischer, Paris (FR)

(73) Assignee: Institut National de la Sante et de la Recherche Medicale (INSERM) (FR)

( * ) Notice: Subject to any disclaimer, the term of this patent is extended or adjusted under 35 U.S.C. 154(b) by 615 days.

(21) Appl. No.: 10/472,277

(22) PCT Filed: Mar. 21, 2002

(86) PCT No.: PCT/IB02/01737

§ 371 (c)(1), (2), (4) Date: Sep. 1, 2004

(87) PCT Pub. No.: WO02/077026

PCT Pub. Date: Oct. 3, 2002

(65) Prior Publication Data

US 2005/0064405 A1 Mar. 24, 2005

(30) Foreign Application Priority Data

Mar. 22, 2001 (WO) ........................ PCT/IB01/00546

(51) Int. Cl.
*C12N 15/11* (2006.01)

(52) U.S. Cl. .................... 536/23.5; 536/23.1; 435/69.1; 435/320.1

(58) Field of Classification Search ........................ None
See application file for complete search history.

(56) References Cited

OTHER PUBLICATIONS

Villartay et al, GenEmbl database Dec. 2000.*

Isogai T. et al., "*Homo sapiens* cDNA FLJ11360 fis", Database EMBL 'Online!, Database accession No. AK021422, XP002184478, Sep. 29, 2000.

Strausberg, R. "*Homo sapiens*, Similar to hypothetical protein FLJ11360", Database EMBL "Online!, Database accession No. BC000863, XP002184479, Mar. 9, 2001.

Hillier L. et al., "au61e08.y1 Schneider fetal brain 00004 *Homo sapiens* cDNA clone", Database EMBL 'Online!, Database accession No. AI929611, XP002184481, Aug. 2, 1999.

Strausberg R., "UI-H-B12-ahk-a-06-0-UI.s NCI_CGAP_Sub4 *Homo sapiens* cDNA clone", Database EMBL "Online!, Database accession No. AW294530, XP002184482, Jan. 17, 2000.

Moshous et al., "A new gene involved in DNA double-strand break repair and V(D)J recombination is located on human chromosome 10p.", Human Molecular Genetics, vol. 9, No. 4, pp. 583-588, Mar. 1, 2000.

Difilippantonio, Michael J. et al., "DNA repair protein Ku80 suppresses chromosomal aberrations and malignant transformation", Nature, vol. 404, No. 6777, pp. 510-514, Mar. 30, 2000.

Liber, Michael R. "The biochemistry and biological significance of nonhomologous DNA end joining: An essential repair process in multicellular eukaryotes", Genes to Cells, vol. 4, No. 2, pp. 77-82, Feb. 2, 1999.

Moshous, Despina et al., "Artemis, a novel DNA double-strand break repair/V(D)J recombination protein, is mutated in human sever combined immune deficiency", Cell, vol. 105, No. 2, pp. 177-186, Apr. 20, 2001.

* cited by examiner

*Primary Examiner*—Q. Janice Li
(74) *Attorney, Agent, or Firm*—Lerner, David, Littenberg, Krumholz & Mentlik, LLP

(57) ABSTRACT

The invention related to a new gene and protein involved in V(D)J recombination and/or DNA repair. The invention also relates to methods of diagnosis and therapy using these gene and protein. The invention also relates to transgenic animals over- or under-expressing said gene.

10 Claims, 1 Drawing Sheet

SEQUENCE LISTING

<160> NUMBER OF SEQ ID NOS: 35

<210> SEQ ID NO 1
<211> LENGTH: 2354
<212> TYPE: DNA
<213> ORGANISM: Homo sapiens
<220> FEATURE:
<223> OTHER INFORMATION: Encoding sequence: nucleotides 36 to 2114 or 60 to 2114.

<400> SEQUENCE: 1

```
gcggttttgg ggtcccggac tctgggatcg gcggcgctat gagttctttc gaggggcaga       60
tggccgagta tccaactatc tccatagacc gcttcgatag ggagaacctg agggcccgcg      120
cctacttcct gtcccactgc cacaaagatc acatgaaagg attaagagcc cctaccttga      180
aaagaaggtt ggagtgcagc ttgaaggttt atctatactg ttcacctgtg actaaggagt      240
tgttgttaac gagcccgaaa tacagatttt ggaagaaacg aattatatct attgaaatcg      300
agactcctac ccagatatct ttagtggatg aagcatcagg agagaaggaa gagattgttg      360
tgactctctt accagctggt cactgtccgg atcagttat gtttttattt cagggcaata      420
atggaactgt cctgtacaca ggagacttca gattggcgca aggagaagct gctagaatgg      480
agcttctgca ctccggggc agagtcaaag acatccaaag tgtatatttg gatactacgt      540
tctgtgatcc aagattttac caaattccaa gtcgggagga gtgtttaagt ggagtcttag      600
agctggtccg aagctggatc actcggagcc cgtaccatgt tgtgtggctg aactgcaaag      660
cggcttatgg ctatgaatat tgttcacca accttagtga agaattagga gtccaggttc      720
atgtgaataa gctagacatg tttaggaaca tgcctgagat ccttcatcat ctcacaacag      780
accgcaacac tcagatccat gcatgccggc atcccaaggc agaggaatat tttcagtgga      840
gcaaattacc ctgtggaatt acttccagaa atagaattcc actccacata atcagcatta      900
agccatccac catgtggttt ggagaaagga gcagaaaaac aaatgtaatt gtgaggactg      960
gagagagttc atacagagct tgttttttctt ttcactcctc ctacagtgag attaaagatt     1020
tcttgagcta cctctgtcct gtgaacgcat atccaaatgt cattccagtt ggcacaacta     1080
tggataaagt tgtcgaaatc ttaaagcctt tatgccggtc ttcccaaagt acggagccaa     1140
agtataaacc actgggaaaa ctgaagagag ctagaacagt tcaccgagac tcagaggagg     1200
aagatgacta tctctttgat gatcctctgc caatacctt aaggcacaaa gttccatacc     1260
cggaaacttt tcaccctgag gtattttcaa tgactgcagt atcagaaaag cagcctgaaa     1320
aactgagaca aaccccagga tgctgcagag cagagtgtat gcagagctct cgtttcacaa     1380
actttgtaga ttgtgaagaa tccaacagtg aaagtgaaga agaagtagga atcccagctt     1440
cactgcaagg agatctgggc tctgtacttc acctgcaaaa ggctgatggg gatgtacccc     1500
agtgggaagt attctttaaa agaaatgatg aaatcacaga tgagagtttg gaaaacttcc     1560
cttcctccac agtggcaggg ggatctcagt caccaaagct tttcagtgac tctgatggag     1620
aatcaactca catctcctcc cagaattctt cccagtcaac acacataaca gaacaaggaa     1680
gtcaaggctg ggacagccaa tctgatactg ttttggtatc ttcccaagag agaaacagtg     1740
gggatattac ttccttggac aaagctgact acagaccaac aatcaaagag aatattcctg     1800
cctctctcat ggaacaaaat gtaatttgcc caaaggatac ttactccgat ttgaaaagca     1860
gagataaaga tgtgacaata gttcctagta ctggagaacc aactactcta agcagtgaga     1920
cacatatacc cgaggaaaaa gtttgctaa atcttagcac aaatgcagat tcccagagct     1980
cttctgattt tgaagttccc tcaactccag aagctgagtt acctaaacga gagcatttac     2040
aatatttata tgagaagctg gcaactggtg agagtatagc agtcaaaaaa agaaaatgct     2100
cactcttaga tacctaagaa ttcaaagcgt ttcaacctag agcaaccact aaaaaacctg     2160
cacagagatg acagtcaata ttacaataga gaaaatacag tacttaaaaa tgttcaaata     2220
acctggttgg gtgtggtggc tcacacttgt aatcccagca ctttgaggtg gcaatggct     2280
tgagcccagg agttcgacac cagcctggcc aacacagtga attgtgtctc tacttccaaa     2340
```
aaaaaaaaaa aaaa                                                          2354

<210> SEQ ID NO 2
<211> LENGTH: 692
<212> TYPE: PRT
<213> ORGANISM: Homo sapiens
<220> FEATURE:
<223> OTHER INFORMATION: Alternative site of protein's start: Met8

<400> SEQUENCE: 2

Met Ser Ser Phe Glu Gly Gln Met Ala Glu Tyr Pro Thr Ile Ser Ile
  1               5                  10                  15

Asp Arg Phe Asp Arg Glu Asn Leu Arg Ala Arg Ala Tyr Phe Leu Ser
             20                  25                  30

His Cys His Lys Asp His Met Lys Gly Leu Arg Ala Pro Thr Leu Lys
         35                  40                  45

Arg Arg Leu Glu Cys Ser Leu Lys Val Tyr Leu Tyr Cys Ser Pro Val
     50                  55                  60

Thr Lys Glu Leu Leu Leu Thr Ser Pro Lys Tyr Arg Phe Trp Lys Lys
 65                  70                  75                  80

Arg Ile Ile Ser Ile Glu Ile Glu Thr Pro Thr Gln Ile Ser Leu Val
                 85                  90                  95

Asp Glu Ala Ser Gly Glu Lys Glu Ile Val Val Thr Leu Leu Pro
            100                 105                 110

Ala Gly His Cys Pro Gly Ser Val Met Phe Leu Phe Gln Gly Asn Asn
        115                 120                 125

Gly Thr Val Leu Tyr Thr Gly Asp Phe Arg Leu Ala Gln Gly Glu Ala
    130                 135                 140

Ala Arg Met Glu Leu Leu His Ser Gly Gly Arg Val Lys Asp Ile Gln
145                 150                 155                 160

Ser Val Tyr Leu Asp Thr Thr Phe Cys Asp Pro Arg Phe Tyr Gln Ile
                165                 170                 175

Pro Ser Arg Glu Glu Cys Leu Ser Gly Val Leu Glu Leu Val Arg Ser
            180                 185                 190

Trp Ile Thr Arg Ser Pro Tyr His Val Val Trp Leu Asn Cys Lys Ala
        195                 200                 205

Ala Tyr Gly Tyr Glu Tyr Leu Phe Thr Asn Leu Ser Glu Glu Leu Gly
    210                 215                 220

Val Gln Val His Val Asn Lys Leu Asp Met Phe Arg Asn Met Pro Glu
225                 230                 235                 240

Ile Leu His His Leu Thr Thr Asp Arg Asn Thr Gln Ile His Ala Cys
                245                 250                 255

Arg His Pro Lys Ala Glu Glu Tyr Phe Gln Trp Ser Lys Leu Pro Cys
            260                 265                 270

Gly Ile Thr Ser Arg Asn Arg Ile Pro Leu His Ile Ile Ser Ile Lys
        275                 280                 285

Pro Ser Thr Met Trp Phe Gly Glu Arg Ser Arg Lys Thr Asn Val Ile
    290                 295                 300

Val Arg Thr Gly Glu Ser Ser Tyr Arg Ala Cys Phe Ser Phe His Ser
305                 310                 315                 320

Ser Tyr Ser Glu Ile Lys Asp Phe Leu Ser Tyr Leu Cys Pro Val Asn
                325                 330                 335

Ala Tyr Pro Asn Val Ile Pro Val Gly Thr Thr Met Asp Lys Val Val
            340                 345                 350

```
Glu Ile Leu Lys Pro Leu Cys Arg Ser Ser Gln Ser Thr Glu Pro Lys
        355                 360                 365

Tyr Lys Pro Leu Gly Lys Leu Lys Arg Ala Arg Thr Val His Arg Asp
        370                 375                 380

Ser Glu Glu Asp Asp Tyr Leu Phe Asp Pro Leu Pro Ile Pro
385                 390                 395                 400

Leu Arg His Lys Val Pro Tyr Pro Glu Thr Phe His Pro Glu Val Phe
                405                 410                 415

Ser Met Thr Ala Val Ser Glu Lys Gln Pro Glu Lys Leu Arg Gln Thr
                420                 425                 430

Pro Gly Cys Cys Arg Ala Glu Cys Met Gln Ser Ser Arg Phe Thr Asn
                435                 440                 445

Phe Val Asp Cys Glu Glu Ser Asn Ser Glu Ser Glu Glu Val Gly
                450                 455                 460

Ile Pro Ala Ser Leu Gln Gly Asp Leu Gly Ser Val Leu His Leu Gln
465                 470                 475                 480

Lys Ala Asp Gly Asp Val Pro Gln Trp Glu Val Phe Phe Lys Arg Asn
                485                 490                 495

Asp Glu Ile Thr Asp Glu Ser Leu Glu Asn Phe Pro Ser Ser Thr Val
                500                 505                 510

Ala Gly Gly Ser Gln Ser Pro Lys Leu Phe Ser Asp Ser Asp Gly Glu
                515                 520                 525

Ser Thr His Ile Ser Ser Gln Asn Ser Ser Gln Ser Thr His Ile Thr
                530                 535                 540

Glu Gln Gly Ser Gln Gly Trp Asp Ser Gln Ser Asp Thr Val Leu Val
545                 550                 555                 560

Ser Ser Gln Glu Arg Asn Ser Gly Asp Ile Thr Ser Leu Asp Lys Ala
                565                 570                 575

Asp Tyr Arg Pro Thr Ile Lys Glu Asn Ile Pro Ala Ser Leu Met Glu
                580                 585                 590

Gln Asn Val Ile Cys Pro Lys Asp Thr Tyr Ser Asp Leu Lys Ser Arg
                595                 600                 605

Asp Lys Asp Val Thr Ile Val Pro Ser Thr Gly Glu Pro Thr Thr Leu
                610                 615                 620

Ser Ser Glu Thr His Ile Pro Glu Glu Lys Ser Leu Leu Asn Leu Ser
625                 630                 635                 640

Thr Asn Ala Asp Ser Gln Ser Ser Asp Phe Glu Val Pro Ser Thr
                645                 650                 655

Pro Glu Ala Glu Leu Pro Lys Arg Glu His Leu Gln Tyr Leu Tyr Glu
                660                 665                 670

Lys Leu Ala Thr Gly Glu Ser Ile Ala Val Lys Lys Arg Lys Cys Ser
                675                 680                 685

Leu Leu Asp Thr
        690

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer
      0083F1

<400> SEQUENCE: 3
gatcggcggc gctatgagtt                                                    20
```

```
<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer 169F

<400> SEQUENCE: 4
tgtcatctct gtgcaggttt                                            20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer
      Ex1F1.

<400> SEQUENCE: 5
ctccggactc ctctgattgg                                            20

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Primer
      Ex1R1

<400> SEQUENCE: 6
gggacaaggc gtgtgct                                               17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Primer
      Ex2F1

<400> SEQUENCE: 7
acttgcagaa gaaagag                                               17

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer
      Ex2R1

<400> SEQUENCE: 8
agtgtatttg gtaggattat                                            20

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Primer
      Ex3F1

<400> SEQUENCE: 9
attttgtgcc agcgtaa                                               17

<210> SEQ ID NO 10
```

```
<211> LENGTH: 20
<212> TYPE: DNA
<213> ORGANISM: Artificial Sequence
<220> FEATURE:
<223> OTHER INFORMATION: Description of Artificial Sequence: Primer
      Ex3R1

<400> SEQUENCE: 10
atgaactcct gacctcaagt                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer
      Ex4F1

<400> SEQUENCE: 11
actttacaat tctttctgtt                                                 20

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Primer
      Ex4R1

<400> SEQUENCE: 12
tgagcattca aaatca                                                     16

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer
      Ex5F1

<400> SEQUENCE: 13
aaggattcca cttgtttcta                                                 20

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Primer
      Ex5R1

<400> SEQUENCE: 14
tgcagcctcc aactc                                                      15

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Primer
      Ex6F1

<400> SEQUENCE: 15
cgagggaaga ggtgacag                                                   18

<210> SEQ ID NO 16
<211> LENGTH: 20
```

```
<212> TYPE: DNA
<213> ORGANISM: Artificial Sequence
<220> FEATURE:
<223> OTHER INFORMATION: Description of Artificial Sequence: Primer
      Ex6R1

<400> SEQUENCE: 16 aaacccatc tccactaaaa                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer
      Ex7F1

<400> SEQUENCE: 17
atagttggga ggctgaggta                                              20

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Primer
      Ex7R2

<400> SEQUENCE: 18
cacctacggg gacagtt                                                 17

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Primer
      Ex8F2

<400> SEQUENCE: 19
atatcctaac tgtccccgta g                                            21

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Primer
      Ex8R1

<400> SEQUENCE: 20
ggccaacatg gtgaaatg                                                18

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer
      Ex9F1

<400> SEQUENCE: 21
gcactgaata gccaaaaact                                              20

<210> SEQ ID NO 22
<211> LENGTH: 17
<212> TYPE: DNA
```

```
<213> ORGANISM: Artificial Sequence
<220> FEATURE:
<223> OTHER INFORMATION: Description of Artificial Sequence: Primer
      Ex9R1

<400> SEQUENCE: 22
gcctagatcg caccact                                                      17

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer
      Ex10F1

<400> SEQUENCE: 23
ttgagactct gcctacaaca                                                   20

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Primer
      Ex10R1

<400> SEQUENCE: 24
tagcatcccc tccattta                                                     18

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Primer
      Ex11F1

<400> SEQUENCE: 25
cacacgcggt ctacaa                                                       16

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Primer
      Ex11R1

<400> SEQUENCE: 26
ggggactacc tgtcaactac                                                   20

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Primer
      Ex12F1

<400> SEQUENCE: 27
ggagatcttt gggagtgag                                                    19

<210> SEQ ID NO 28
<211> LENGTH: 20
<212> TYPE: DNA
<213> ORGANISM: Artificial Sequence
```

```
<220> FEATURE:
<223> OTHER INFORMATION: Description of Artificial Sequence: Primer
      Ex12R1

<400> SEQUENCE: 28
acctctcaat tctgccacac                                                  20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Primer
      Ex13F1

<400> SEQUENCE: 29
atttgccact ttattacatc                                                  20

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Primer
      Ex13R1

<400> SEQUENCE: 30
gcaaagtact tcctgagac                                                   19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Primer
      Ex 14F1

<400> SEQUENCE: 31
agattggcct ccctattct                                                   19

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer
      Ex14R1

<400> SEQUENCE: 32
ccaaccaggt tatttgaaca                                                  20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Primer
      0083F4

<400> SEQUENCE: 33
agccaaagta taaaccactg                                                  20

<210> SEQ ID NO 34
<211> LENGTH: 12
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 34
aggtacgtgt gc                                                           12

<210> SEQ ID NO 35
<211> LENGTH: 6
<212> TYPE: PRT
<213> ORGANISM: Homo sapiens
<220> FEATURE:
<221> NAME/KEY: MOD_RES
<222> LOCATION: (2)
<223> OTHER INFORMATION: Variable amino acid

<400> SEQUENCE: 35

His Xaa His Lys Asp His
 1               5
```

GENE INVOLVED IN V(D)J RECOMBINATION AND/OR DNA REPAIR

FIELD OF THE INVENTION

The present invention relates to a novel DNA sequence that is involved in V(D)J recombination in lymphocytes, and the mutation of which causes Severe Combined Immunodeficiencies (SCID). The invention also relates to methods of diagnosis, methods of therapy, and methods of screening of new compounds using this sequence, as well as to transgenic animals.

BACKGROUND OF THE INVENTION

B and T lymphocytes recognize foreign antigen through specialized receptors: the immunoglobulins and the T cell receptor (TCR) respectively. The highly polymorphic antigen-recognition regions of these receptors are composed of variable (V), diversity (D), and joining (J) gene segments which undergo somatic rearrangement prior to their expression by a mechanism known as V(D)J recombination (Tonegawa, 1983). Each V, D, and J segment is flanked by Recombination Signal Sequences (RSSs) composed of conserved heptamers and nonamers separated by random sequences of either 12 or 23 nucleotides. RSSs serve as recognition sequences for the V(D)J Recombinase.

V(D)J recombination can be roughly divided into three steps. The RAG1 and RAG2 proteins initiate the rearrangement process through the recognition of the RSS and the introduction of a DNA double strand break (dsb) at the border of the heptamer (Schatz et al., 1989; Oettinger, 1990). RAG1 and RAG2 are the sole two factors required to catalyze DNA cleavage in cell-free systems (McBlane et al., 1995; Van Gent et al., 1995; Eastman et al., 1996) in a reaction reminiscent of retroviral integration and transposition (van Gent et al., 1996; Roth and Craig, 1998). Three acidic residues, DDE, were shown to compose the active site carried by RAG1 (Kim et al., 1999; Landree et al., 1999; Fugmann et al., 2000). The restricted expression of both RAG1 and RAG2 genes to immature B and T lymphocytes confines V(D)J recombination to the lymphoid lineage. At the end of this phase, which causes a DNA damage, the chromosomal DNA is left with two hairpin-sealed coding ends (CE), while the RSSs and the DNA intervening sequences are excised from the chromosome as blunt, phosphorylated signal ends (SE) (Roth et al., 1992; Schlissel et al., 1993; Zhu and Roth, 1995). The subsequent step consists in recognition and signaling of the DNA damage to the DNA repair machinery. From now on, ubiquitous enzymatic activities are involved.

The description of the murine scid situation, characterized by a lack of circulating mature B and T lymphocytes (Bosma et al., 1983), as a general DNA repair defect accompanied by an increased sensitivity to ionizing radiation or other agents causing DNA dsb provided the link between V(D)J recombination and DNA dsb repair (Fulop, 1990; Biedermann, 1991; Hendrickson, 1991). This was further confirmed by the analysis of Chinese ovary cell lines (CHO), initially selected on the basis of their defect in DNA repair, which turned out to have impaired V(D)J recombination in vitro (Taccioli et al., 1993). This led to the description of the Ku70/Ku80/DNA-PKcs complex as a DNA damage sensor (review in (Jackson and Jeggo, 1995)). Briefly, DNA-PKcs is a DNA-dependant protein kinase that belongs to the Phosphoinositol (PI) kinase family, which is recruited at the site of the DNA lesion through the interaction with the regulatory complex Ku70/80 that binds to DNA ends (Gottlieb and Jackson, 1993). Cells from scid mice lack DNA-PK activity owing to a mutation in the DNA-PKcs encoding gene (Blunt et al., 1996; Danska et al., 1996). This severely compromises the V(D)J recombination process, ultimately leading to an arrest in both B and T cell development.

More recently, two other proteins, NBS1 and γ-H2AX, have been identified on the site of chromosomal rearrangement in the TCR-α locus in thymocytes (Chen et al., 2000). NBS 1, which is mutated in the Nijmegen breakage syndrome, participates in the formation of the RAD50/MRE11/NBS1 complex involved in DNA repair (Carney et al., 1998; Varon et al., 1998). γ-H2AX represents the phosphorylated form of histone H2A in response to external damage and is considered as an important sensor of DNA damage (Rogakou et al., 1998; Rogakou et al., 1999; Paull et al., 2000). The biological implication of this observation is not yet fully understood, but it indicates that the RAD50/MRE11/NBS1 complex may cooperate with the DNA-PK complex in sensing and signaling the RAG1/2-mediated DNA dsb to the cellular DNA repair machinery. In the final phase of the V(D)J rearrangement, the DNA-repair machinery per se will ensure the re-ligation of the two chromosomal broken ends. This last step resembles the well-known DNA non-homologous end joining (NHEJ) pathway in the yeast *Sacchaomyces cerevisiae* (review in (Haber, 2000)) and involves the XRCC4 (Li et al., 1995) and the DNA-Ligase IV (Robins and Lindahl, 1996) factors. The crystal structure recently obtained for XRCC4 demonstrates the dumb-bell like conformation of this protein and provides a structural basis for its binding to DNA as well as its association with DNA-Ligase IV (Junop et al., 2000). All the animal models carrying a defective gene of either one of the known V(D)J recombination factors, either natural (murine and equine scid) or engineered through homologous recombination, have a profound defect in the lymphoid developmental program owing to an arrest of the B and T cell maturation at early stages (Mombaerts et al., 1992; Shinkai et al., 1992; Nussenzweig et al., 1996; Zhu et al., 1996; Jhappan et al., 1997; Shin et al., 1997; Barnes et al., 1998; Frank et al., 1998; Gao et al., 1998; Gao et al., 1998; Taccioli et al., 1998). In the cases of DNA-LigaseIV and XRCC4 this phenotype is also accompanied by an early embryonic lethality caused by massive apoptotic death of postmitotic neurons (Barnes et al., 1998; Frank et al., 1998; Gao et al., 1998).

In humans, several immune deficiency conditions are characterized by faulty T and/or B cell developmental program (Fischer et al., 1997). In about 20% of the cases, the severe combined immunodeficiency (SCID) phenotype is caused by a complete absence of both circulating B and T lymphocytes, associated with a defect in the V(D)J recombination process, while Natural Killer (NK) cells are present. Mutations in either the RAG1 or RAG2 gene account for a subset of patients with this condition (Schwarz et al., 1996; Comeo et al., 2000; Villa et al., 2001). In some patients (RS-SCID), the T-B-SCID defect is not caused by RAG1 or RAG2 mutations and is accompanied by an increased sensitivity to ionizing radiations of both bone marrow cells (CFU-GMs) and primary skin fibroblasts (Cavazzana-Calvo et al., 1993), as well as a defect in V(D)J recombination in fibroblasts (Nicolas et al., 1998).

Although this condition suggests that RS-SCID could have a general DNA-repair defect reminiscent of the murine scid situation, DNA-PK activity was found normal in these patients and the implication of the DNA-PKcs gene has been unequivocally ruled out by genetic means in several consanguineous families (Nicolas et al., 1996). A role for all the other known genes involved in V(D)J recombination/DNA repair was equally excluded as being responsible for RS-SCID condition (Nicolas et al., 1996). The gene defective in RS-SCID therefore encodes a yet undescribed factor. The inventors recently assigned the disease related locus to the short arm of human chromosome 10, in a 6.5 cM region delimited by two polymorphic markers D10S1664 and D10S674 (Moshous et al., 2000), a region shown to be linked to a similar SCID condition described in Athabascan speaking American Indians (A-SCID) (Hu et al., 1988; Li et al., 1998).

SUMMARY OF THE INVENTION

The present invention relates to the identification and cloning of the Artemis gene, localized in this region of Chromosome 10. Artemis codes for a novel V(D)J recombination and/or DNA repair factor that belongs to the metallo β-lactamase superfamily and whose mutations give rise to the human RS-SCID condition.

In particular, the present invention relates to an isolated nucleic acid molecule selected from the group consisting of:
 a) SEQ ID No 1, nucleotides 39-2114 of SEQ ID No 1, or nucleotides 60-2114 of SEQ ID No 1
 b) an isolated and purified nucleic acid comprising the nucleic acid of a)
 c) an isolated nucleic acid that specifically hybridizes under (highly) stringent conditions to the complement of the nucleic acid of a) (under high stringency conditions of 0.2×SSC and 0.1% SDS at 55-65° C.), preferably wherein said nucleic acid encodes a protein that is involved in the V(D)J recombination and/or DNA repair
 d) an isolated nucleic acid having at least 80% homology with the nucleic acid of a), preferably over the full length of SEQ ID No 1, and preferably wherein said nucleic acid encodes a protein that is involved in the V(D)J recombination and/or DNA repair
 e) a fragment of the nucleic acid of a) comprising at least 15 nucleotides, with the proviso that said fragment is not entirely comprised between nucleotides 158-609, 607-660, or 29-537 of SEQ ID No 1.

The present invention also relates to the polypeptides coded by the nucleic acid of the invention and to different uses that can be made with the objects of the invention.

DESCRIPTION OF THE PREFERRED EMBODIMENTS

Figure 1:
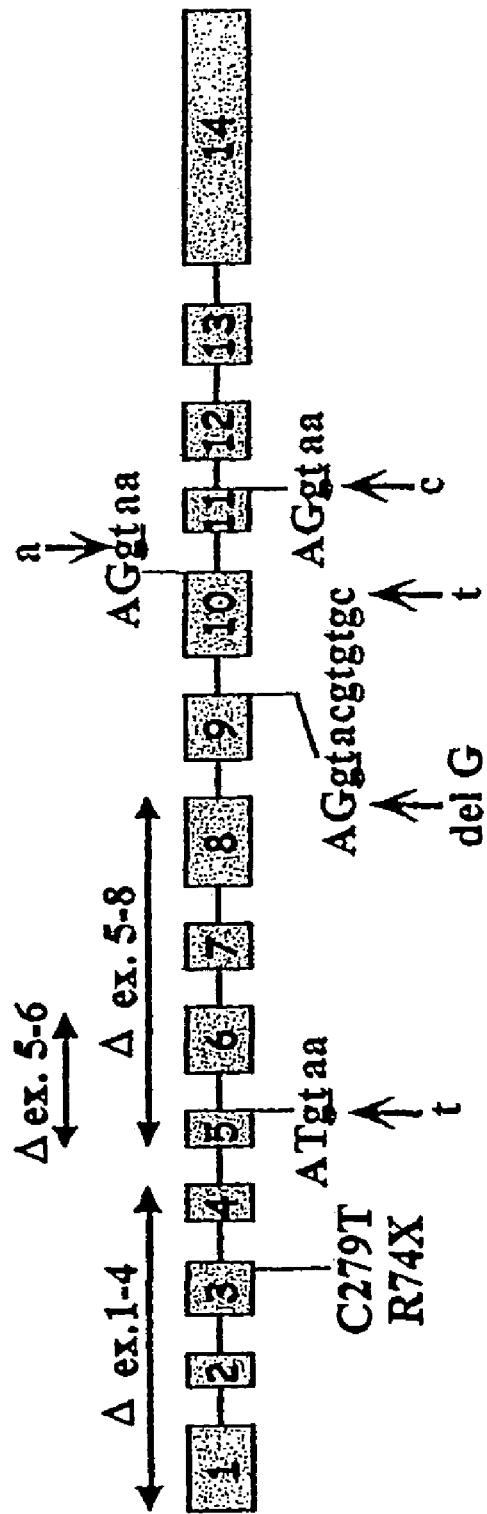
FIG. 1 represents a schematic view of the genomic organization of the Artemis gene, with the exons represented as rectangles, and the different mutations identified in RS-SCID patients. The 12-mer nucleotide seuuence is shown in SEQ ID NO: 34.

In a first aspect, the present invention relates to an isolated nucleic acid molecule selected from the group consisting of:
 a) SEQ ID No 1 nucleotides 39-2114 of SEQ ID No 1, or nucleotides 60-2114 of SEQ ID No 1,
 b) an isolated nucleic acid comprising the nucleic acid of a),
 c) an isolated nucleic acid that specifically hybridizes under stringent conditions to the complement of the nucleic acid of a),
 d) an isolated nucleic acid having at least 80% homology with the nucleic acid of a),
 e) a fragment of the nucleic acid of a) comprising at least 15 nucleotides, with the proviso that said fragment is not entirely comprised between nucleotides 158-609, 607-660, or 29-537 of SEQ ID No 1.

It is also envisioned that the invention encompasses the genomic nucleic acid sequence that leads to SEQ ID No 1 after transcription. The genomic nucleic acid sequence can easily be obtained from SEQ ID No 1 by the person skilled in the art by screening a library of genomic DNA, using a probe derived from SEQ ID No 1. It may also be obtained starting from the sequence, having the GenBank accession number AL360083 that may be available at the following address: http://www.ncbi.nlm.nih.gov:80/entrez/query.fcgi?cmd=Retrieve&db=Nucleotide&list_uids=112584428&dopt=GenBank.

The invention also encompasses an isolated nucleic acid molecule that is the complement of the isolated nucleic acid molecule of the invention, as described above.

In a preferred embodiment, the nucleic acid of c) specifically hybridizes under highly stringent conditions to the complement of the nucleic acid of a) (for example under high stringency conditions of 0.2×SSC and 0.1% SDS at 55-65° C., or under conditions as described below), and in a preferred embodiment, encodes a protein that has a biological activity of V(D)J recombination and/or DNA repair.

In other embodiments, the nucleic acid of d) harbors 85, 90, 95, 98 or 99% homology with the nucleic acid of a). The homology is preferably calculated over the full length of SEQ ID No 1 or nucleotides 39-2114 of SEQ ID No 1. In a preferred embodiment, said nucleic acid encodes a protein that has a biological activity of V(D)J recombination and/or DNA repair.

By nucleic acid, nucleic sequence, nucleic acid sequence, polynucleotide, oligonucleotide, polynucleotide sequence, nucleotidic sequence, all terms that will be indifferently used in the present application, one designates a specific string of nucleotides, modified or not, that defines a fragment or region of a nucleic acid, comprising natural or non-natural nucleotides. It may be a double strand DNA, a single strand DNA, or transcription products of said dans. The sequences according to the invention also comprise Peptid Nucleic Acid, or analogs, or sequences with modified nucleotides (phosphorothioates, methylphosphonates . . . ).

By isolated, it is meant that the nucleic acid of the invention is not in its natural chromosomal environment. The sequences according to the invention have been isolated and/or purified, meaning that they have been directly or indirectly obtained (for example by copy through amplification), their natural environment being at least partially modified. The nucleic acids that have been obtained through chemical synthesis are also part of the present invention.

The stringent hybridization conditions may be defined as described in Sambrook et al. ((1989) Molecular cloning: a laboratory manual. $2^{nd}$ Ed. Cold Spring Harbor Lab., Cold Spring Harbor, N.Y.), with the following conditions: 5× or 6×SCC, 50-65° C. Highly stringent conditions that can also be used for hybridization are defined with the following conditions: 6×SSC, 60-65° C.

Hybridization ADN-ADN or ADN-ARN may be performed in two steps: (1) prehybridization at 42° C. pendant 3 h in phosphate buffer (20 mM, pH 7.5) containing 5 or 6×SSC (1×SSC corresponding to a solution 0.15 M NaCl+0.015 M sodium citrate), 50% formamide, 7% sodium dodecyl sulfate (SDS), 10× Denhardt's, 5% dextran sulfate et 1% salmon sperm DNA; (2) hybridization during up to 20 at a temperature of 50-65° C., more preferably 60-65° C. followed by different washes (about 20 minutes at in 2×SSC+2% SDS, then 0.1×SSC+0.1% SDS). The last wash is performed in 0.2×SSC+0.1% SDS for about 30 minutes at about 50-65° C., and/or in 0.1×SSC+0.1% SDS at the same temperature. These high stringency hybridization conditions may be adapted by a person skilled in the art. Indeed, the person skilled in the art is able to determine the best stringency conditions by varying the concentrations in SSC and SDS and the temperature of hybridization and washings.

The term "conditions of high stringency" also refers to hybridization and washing under conditions that permit binding of a nucleic acid molecule used for screening, such as an oligonucleotide probe or cDNA molecule probe, to highly homologous sequences. An exemplary high stringency wash solution is 0.2×SSC and 0.1% SDS used at a temperature of between 50-65° C.

Where oligonucleotide probes are used to screen cDNA or genomic libraries, one of the following two high stringency solution may be used. The first of these is 6×SSC with 0.05% sodium pyrophosphate at a temperature of 35° C.-62° C., depending on the length of the oligonucleotide probe. For example, 14 base pair probes are washed at 35° C.-40° C., 17 base pair probes are washed at 45° C.-50° C., 20 base pair probes are washed at 52° C.-57° C., and 23 base pair probes are washed at 57-63° C. The temperature can be increased 2-3° C. where the background non-specific binding appears high. A second high stringency solution utilizes tetramethylammonium chloride (TMAC) for washing oligonucleotide probes. One stringent washing solution is 3 M TMAC, 50 mM Tris-HCl, pH 8.0, and 0.2% SDS. The washing temperature using this solution is a function of the length of the probe. For example, a 17 base pair probe is washed at about 45-50° C.

Two polynucleotides are said to be "identical" or "homologous" if the sequence of nucleotides or amino acid residues, respectively, in the two sequences is the same when aligned for maximum correspondence as described below. The term "complementary to" is used herein to mean that the complementary sequence is identical to all or a specified contiguous portion of a reference polynucleotide sequence. Sequence comparisons between two (or more) polynucleotides or polypeptides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *Ad. App. Math* 2: 482 (1981), by the homology alignment algorithm of Neddleman and Wunsch, *J. Mol. Biol.* 48:443 (1970), by the search for similarity method of Pearson and Lipman, *Proc. Natl. Acad. Sci.* (U.S.A.) 85:2444 (1988), by computerized implementation of these algorithms (GAP, BESTFIT, BLAST N, BLAST P, FASTA, and TFASTA in the Wisconsin Genetics Software Package, Genetics Computer Group (GCG), 575 Science Dr., Madison, Wis.), or by inspection. In order to determine the optimal window of alignment, the BLAST program could be used, using matrix BLOSUM 62, or matrices PAM or PAM250, with the default parameters, or parameters modified in order to increase the specificity.

"Percentage of sequence identity or homology" is determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The nucleic acid of d) presents an homology of at least 80%, more preferably 90%, more preferably 95%, more preferably 98%, the most preferable being 99% with the nucleic acid of a).

Preferred nucleic acids contain a mutation in the codons corresponding the Histidine and the Aspartic Acid residues, that are located between nucleotides 39-488, 60-488, 39-1193 and 60-1193.

A preferred acid nucleic contains a mutation at one nucleotide chosen in the group consisting of nucleotides 87, 88, 89, 141, 142, 143, 147, 148, 149, 150, 151, 152, 444, 445, 446, 489, 490, 491, 531, 532, 533, 993, 994 and 995 of SEQ ID No 1.

A preferred nucleic acid contains a mutation at one nucleotide chosen in the group consisting of nucleotides 150, 151, 152, 489, 490, and 491 od SEQ ID No 1.

The fragment of the nucleic acid of a) contain at least 15 bases, more preferably 25, 50, 60, 75, 100, 150, 200, 250, 300, 400, 500, 600, 750, 1000, 1250, 1500, 2000 bases. This fragments may be used as primers for amplification, or as probes especially when looking for homologous DNA or DNA hybridizing with the nucleic acid of a). These fragments may also be labeled.

The different labels that may be used are well known to the person skilled in the art, and one can cite $^{32}$P, $^{33}$P, $^{35}$S, $^{3}$H or $^{125}$I. Non radioactive labels may be selected from ligants as biotin, avidin, streptavidin, dioxygenin, haptens, dyes, luminescent agents like radioluminescent, chemoluminescent, bioluminescent, fluorescent or phosphorescent agents.

The fragments according to the invention are preferably biologically active, i.e. they harbor the same biological activity than the native protein coded by nucleotides 39-2114 of SEQ ID No 1, or nucleotides 60-2114 of SEQ ID No 1. This protein is involved in V(D)J recombination and/or DNA repair, and the tests that can be used by the person skilled in the art to assess these activities are well known, one of them being described in the examples.

The most preferred fragments of the nucleic acid of a) are the fragments coding for a protein or a polypeptide (nucleotides 39-2114 or 60-2114 of SEQ ID No 1). One can also cite the nucleotides 1-38, and 2115-2354 of SEQ ID No 1 that may contain regulatory sequences (promoters, enhancers . . . ). Another interesting fragment is the fragment coding for a metallo-β-lactamase region (39-488).

The inventors have also demonstrated that it is possible to obtain the V(D)J recombination activity, by using only a fragment of the protein, that is coded by nucleotides 39-1193 or 60-1193. This specific fragment is also preferred in the present invention.

Interesting fragments are also the fragments corresponding to the exons, i.e. corresponding, in SEQ ID No 1, to nucleotides 1-147, 39-147, 148-199, 200-284, 285-344, 345-400, 401-502, 503-575, 576-716, 717-818, 819-955, 956-1010, 1011-1099, 1100-1194, 1195-2114, 1195-2354, but also the fragments corresponding to nucleotides 1-199, 1-284, 1-344, 1-400, 1-502, 1-575, 1-716, 1-818, 1-955, 1-1010, 1-1099, 1-1194, 1-2114, 39-199, 39-284, 39-344, 39-400, 39-502, 39-575, 39-716, 39-818, 39-955, 39-1010, 39-1099, 39-1194, 39-2354, 60-199, 60-284, 60-344, 60-400, 60-502, 60-575, 60-716, 60-818, 60-955, 60-1010, 60-1099, 60-1194, 60-2354, 148-284, 148-344, 148-400, 148-502, 148-575, 148-716, 148-818, 148-955, 148-1010, 148-1099, 148-1194, 148-2114, 148-2354, 200-344, 200-400, 200-502, 200-575, 200-716, 200-818, 200-955, 200-1010, 200-1099, 200-1194, 200-2114, 200-2354, 285-400, 285-502, 285-575, 285-716, 285-818, 285-955, 285-1010, 285-1099, 285-1194, 285-2114, 285-2354, 345-502, 345-575, 345-716, 345-818, 345-955, 345-1010, 345-1099, 345-1194, 345-2114, 345-2354, 401-575, 401-716, 401-818, 401-955, 401-1010, 401-1099, 401-1194, 401-2114, 401-2354, 503-716, 503-818, 503-955, 503-1010, 503-1099, 503-1194, 503-2114, 503-2354, 576-818, 576-955, 576-1010, 576-1099, 576-1194, 576-2114, 576-2354, 717-955, 717-1010, 717-1099, 717-1194, 717-2114, 717-2354, 819-1010, 819-1099, 819-1194, 819-2114, 819-2354, 956-1099, 956-1194, 956-2114, 956-2354, 1011-1194, 1011-2114, 1011-2354, 1100-2114, or 1100-2354.

It is important to note that the fragments according to the invention are preferably not entirely comprised between nucleotides 158-609, 607-660, or 29-537 of SEQ ID No 1. Indeed, these nucleotides correspond to EST that have been disclosed in GenBank, under accession numbers AA306797 (nucleotides 29-537) and AA315885 (nucleotides 158-609, 607-660). These EST disclosures are nevertheless incomplete, as AA306797 comprises a "N" in position 91 that makes it unclear, as it represents all 4 different nucleotides (the actual nucleotide is a "C", as seen at position 119 of SEQ ID No 1). Furthermore, AA306797 starts before the first methionin as identified in the present invention (nucleotide 39 of SEQ ID No 1), which does not suggest the actual start codon of the protein of the invention. EST AA315885 possesses a supplemental "C" as compared to the sequence of the invention at nucleotide 453 of AA315885 (corresponding to nucleotide 610 of SEQ ID No 1).

The disclosures of AA306797 and AA315885 have been used by Dronkert et al. (2000, Mol. Cell. Biol., 20, 4553-61) to obtain (after translation of the EST) part of the human SNM1c protein that is partly homologous to the murine SNM1 object of the disclosure. The problems in the two EST that are mentioned above led to a mistaken translated protein.

It is also worth noting that Wood et al. (2001, Science, 291, 1284-9) mention the gene EST corresponding to SNM1C, as being located on chromosome 10, but do not precise the localization (10p), nor do they give any other information than EST AA315885, that was shown to be erroneous.

It is also preferred if the fragments, or the sequence that is complementary to them, according to the invention, are not comprised in their entirety, between nucleotides 1 to 35 and 37 to 189 of SEQ ID No 1. These nucleotides have been disclosed in EST disclosed in GenBank under accession number AA278590, that is incomplete and erroneous, as it misses the "G" nucleotide present on position 36 of SEQ ID No 1.

It is also preferred if the fragments, or the sequence that is complementary to them, according to the invention, are not comprised in their entirety, between nucleotides 1848 to 2321. These nucleotides correspond to some nucleotides present in EST disclosed in GenBank under accession number AI859962, that is incomplete. This EST discloses an erroneous part of the complementary sequence of SEQ ID No1, the nucleotides complementary to the nucleotides present at the start of EST AI859962 do not correspond to the last nucleotides of SEQ ID No1.

This EST contains, in part EST AA278850, that is also incomplete and erroneous (mismatch of a nucleotide as compared with the complement of SEQ ID No 1).

Therefore, these disclosures are not only erroneous and incomplete, but do also not link the nucleic acid of the invention, nor fragments as defined above, to the V(D)J recombination and the SCID deficiency, as did the inventors in the present application. This would have confused the person skilled in the art, which would not have been able to get much information from these disclosures.

The present invention is also drawn to a vector comprising the nucleic acid molecule of the invention, especially the nucleic acid sequence corresponding to nucleotides 39-2114, 60-2114, 39-1193, or 60-1193 of SEQ ID No 1. Numerous vectors are known in the art and they may be, as a matter of examples, expression vectors, or amplification vectors.

The invention is also drawn to a host cell comprising the vector according to the invention.

The invention is also drawn to a process of producing a protein involved in V(D)J recombination and/or DNA repair comprising the steps of:
  a) expressing the nucleic acid molecule according to the invention in a suitable host to synthesize a protein involved in V(D)J recombination and/or DNA repair and
  b) isolating the protein involved in V(D)J recombination and/or DNA repair.

The present invention is also drawn to an isolated nucleic acid molecule that is the complement of the isolated nucleic acid molecule of the invention, as previously defined, and to an isolated protein or peptide coded by the nucleic acid of the invention. As seen below, the protein or peptide of the invention may be obtained either through recombinant DNA, chemical, or other techniques.

The terms polypeptide and protein are to be understood as meaning a specific string of amino-acids that may be natural or synthetic. The person skilled in the art is aware of ways of varying amino-acids. Preferred proteins or polypeptides are especially SEQ ID No 2, and amino-acids 8-692, 1-385 or 8-385 of SEQ ID No 2.

The expression vectors of the invention contain preferably a promoter, traduction initiation and termination signals, as well as appropriate regions for regulating transcription. They need to be maintained in the host cell. The person skilled in the art is aware of such vectors and of the ways to produce and purify proteins, especially by using labels (like Histidine Tag, or glutathione). It is also possible to use in vitro translation kits that are widely available, to produce the protein or peptide according to the invention.

The nucleic acid of the invention or fragment thereof can be inserted into appropriate expression or amplification vector using standard ligation techniques, or homologous recombination. The vector is chosen to allow amplification of the nucleic acid of the invention and/or expression of the gene.

The vectors may be chosen as to be functional in a large variety of hosts, such as prokaryotic, yeast, insect (baculovirus systems) and/or eukaryotic host cells. Selection of the host cell may depend on the properties of the polypeptide or fragment thereof to be expressed, for example if post-traductional modifications are needed (such as glycosylation and/or phosphorylation). If so, eucaryotic cells, such as yeast, insect, or mammalian host cells are preferable.

The person skilled in the art is aware of different types of vectors that may be used, and of the different techniques employed to make them enter the host cells (electroportation, lipofection . . . ).

Reviews of the different usable vectors, host cells and regulatory DNA sequences on the vectors, depending of the host cells may be found in U.S. Pat. No. 6,165,753, in particular columns 9, line 34 to column 13, line 36. This technical part of the document, that relates to the cyclin E2 gene and polypeptide but may be generalized to any other cDNA or gene, is incorporated herein by reference.

Another review of the different vectors, regulatory sequences, host cells, and methods of expression of polypeptides that may be used can be found in WO 99/55730, page 6, line 3 to page 25, line 6, which is herein incorporated by reference.

In summary, the vectors of the invention contain at least one selectable marker gene that encodes a protein necessary for the survival and growth of the host cell in a selective culture medium. Typical selection marker genes encode proteins that either confer resistance to antibiotics such as ampicillin, tetracycline, or kanamycin for prokaryotic host cells, complement auxotrophic deficiencies of the cell (use of urayeasts, for exemple). Preferred selectable markers are the kanamycin resistance gene, the ampicillin resistance gene, and the tetracycline resistance gene. The kanamycine resistance gene is preferred when vectors active both in procaryotic and eucaryotic (mammalian) cells are used, as the protein gives resistance to neomycine in mammalian cells.

The vectors of the invention also contain a ribosome binding sequence such as a Shine-Dalgarno, a Kozak sequence, or an internal ribosome entry site (Ires).

A signal sequence may be also be used to direct the polypeptide out of the host cell where it is synthesized. Many signal sequences are known by persons skilled in the art, and any of them that are functional (homologous or heterologous) in the selected host cell may be used in conjunction with the nucleic sequence according to the invention.

The vectors of the invention are typically derived from a starting vector such as a commercially available vector. Such vectors may or may not contain some of the elements to be included in the completed vector, such elements being introduced by appropriate molecular biology techniques. Thus, the added elements may be individually introduced with the vector after enzymatic digestion and ligation of the element. This procedure is well known in the art and is described for example in Sambrook et al., supra Preferred vectors for which it is possible to start to obtain the vectors of the invention are compatible with bacterial, insect, and mammalian host cells, and include, without being limitative, pCRII, pCR3, and pcDNA3 (Invitrogen Company, San Diego, Calif.), pBSII (Stratagene Company, LaJolla, Calif.), pET15b (Novagen, Madison, Wis.), PGEX (Pharmacia Biotech, Piscataway, N.J.), pEGFP-N2 (Clontech, Palo Alto, Calif.), PETL (BlueBacII; Invitrogen), and pFast-BacDual (Gibco/BRL, Grand Island, N.Y.).

After construction of the vector and insertion of the nucleic acid of the invention, the completed vector may be inserted into a suitable host cell for amplification and/or polypeptide expression.

Such hosts cells may be prokaryotic host cells (such as *E. coli, Bacillus subtilis*) or eukaryotic host cells (such as a yeast cell, an insect cell, or a vertebrate cell). The host cell, when cultured under appropriate conditions, can synthesize the polypeptide which can subsequently be collected from the culture medium (if the host cell secretes it into the medium) or directly from the host cell producing it (if it is not secreted). After collection, the polypeptide can be purified using methods such as molecular sieve chromatography, affinity chromatography, and the like.

Selection of the host cell for the polypeptide production will depend in part on whether the polypeptide is to be glycosylated or phosphorylated (in which case eukaryotic host cells are preferred), and the manner in which the host cell is able to "fold" the protein into its native tertiary structure (e.g., proper orientation of disulfide bridges, etc.) such that biologically active protein is prepared by the cell. When the host cell does not synthesize the polypeptide that has the biological activity of V(D)J recombination and/or DNA repair, the polypeptide may be "folded" after purification, upon various dialysis.

Suitable mammalian cells or cell lines are well known in the art and include Chinese hamster ovary cells (CHO), HeLa, HEK293, Hep-2, 3T3 cells, monkey COS-1 and COS-7 cell lines, and the CV-1 cell line, mouse neuroblastoma N2A cells, HeLa, mouse L-929 cells, 3T3 lines derived from Swiss, Balb-c or NIH mice, BHK or HaK hamster cell lines.

Useful bacterial host cells suitable for the present invention include the various strains of *E. coli*, such as HB101, DH5.α., DH10, or MC1061. Various strains of *B. subtilis, Pseudomonas* spp., other *Bacillus* spp., *Streptomyces* spp., and the like may also be employed in this method.

Many strains of yeast cells known to those skilled in the art are also available as host cells for expression of the polypeptides of the present invention, and one will prefer strains of *Saccharomyces cerevisiae, S. pombe, Kluyveromyces* . . .

Entry (also referred to as "transformation" or "transfection") of the vector into the selected host cell may be achieved using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

The person skilled in the art is aware of the medium to use for cultivation of the host cells, including the selection agent (antibiotic) to add in said medium, depending on the marker that is on the vector inserted into the cell.

The amount of polypeptide produced in the host cell can be evaluated using standard methods known in the art, such as, without limitation, Western blot analysis, SDS-polyacrylamide gel electrophoresis, non-denaturing gel electrophoresis, HPLC separation, immunoprecipitation, and/or activity assays such as DNA binding gel shift assays.

Purification of the polypeptide produced by cells of the invention, when present in solution (secretion or excretion) can be accomplished using a variety of techniques. If it contains a tag such as Hexahistidine, it may essentially be purified in a one-step process by passing the solution through an affinity column where the column matrix has a high affinity for the tag or for the polypeptide directly (Nickel column for poly-histidine).

Where the polypeptide is prepared without a tag attached, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If it is anticipated that the polypeptide will be found primarily intracellularly, the intracellular material (including inclusion bodies for gram-negative bacteria) can be extracted from the host cell using any standard technique known to the person skilled in the art. For example, the host cells can be lysed to release the contents of the periplasm/cytoplasm by French press, homogenization, and/or sonication followed by centrifugation.

If the polypeptide has formed inclusion bodies in the periplasm, the polypeptide is obtained using methods known in the art, especially with the aid of chaotropic agents such as guanidine or urea to release, break apart, and solubilize the inclusion bodies. Further dialysis will help solubilizing the polypeptide.

One can also use other standard methods well known to the skilled artisan, such as separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

In addition to preparing and purifying the polypeptide using recombinant DNA techniques, the polypeptides, fragments, and/or derivatives thereof may be prepared by chemical synthesis methods (such as solid phase peptide synthesis) using techniques known in the art such as those set forth by Merrifield et al., (J. Am. Chem. Soc., 85:2149 [1963]), Houghten et al. (Proc Natl Acad. Sci. USA, 82:5132. [1985]), and Stewart and Young (Solid Phase Peptide Synthesis, Pierce Chemical Co., Rockford, Ill. [1984]). Such polypeptides may be synthesized with or without a methionine on the amino terminus. Chemically synthesized polypeptides or fragments may be oxidized using methods set forth in these references to form disulfide bridges. These synthetic polypeptides or fragments are expected to have biological activity comparable to the polypeptides produced recombinantly or purified from natural sources, namely an ability to promote V(D)J recombination and/or DNA repair and thus may be used interchangably with recombinant or natural polypeptide.

The polypeptide of the invention may be chemically derived, or associated with a polymer. The modified polypeptides according to the invention may have different pharmacological properties than the unmodified polypeptides, such as an increased or a decreased half-time after administration to a animal or human, different pharmacokinetics . . .

The polypeptides according to the invention, their fragments, variants, and/or derivatives may be used to prepare antibodies using standard methods, for example after administration to an animal such as a mouse, a rat, a rabbit or a goat using an appropriate adjuvant (in particular Freund's Complete or Incomplete adjuvant).

Thus, antibodies that react with the polypeptides of the invention, as well as reactive fragments of such antibodies, are also encompassed within the scope of the present invention. The antibodies may be polyclonal, monoclonal, recombinant, chimeric, single-chain and/or bispecific. In preferred embodiment, the antibody or fragment thereof will either be of human origin, or will be "humanized", i.e., prepared so as to prevent or minimize an immune reaction to the antibody when administered to a patient.

The antibody fragment may be any fragment that is reactive with the polypeptides of the present invention the invention also encompasses the hybridomas generated by presenting the polypeptide according to the invention or a fragment thereof as an antigen to a selected mammal, followed by fusing cells (e.g., spleen cells) of the mammal with certain cancer cells to create immortalized cell lines by known techniques, such as the technique of Köhler et Milstein (1975 Nature 256, 495).

The antibodies according to the invention are, for example, chimeric antibodies, humanized antibodies, Fab ou F(ab')$_2$ fragments. They may be immunoconjugates or labeled antibodies.

The inventors of the present invention have demonstrated that the Artemis gene (also named SNM1C) codes for a novel V(D)J recombination and/or DNA repair factor that belongs to the metallo β-lactamase superfamily and whose mutations give rise to the human RS-SCID condition.

Therefore, the present invention is also drawn to a method for the determination of the type of SCID in a patient comprising the step of analyzing the nucleic acid chosen in the group consisting of SEQ ID No 1, nucleotides. 39-2114, 60-2114, 39-1193, and 60-1193 of SEQ ID No 1 in said patient, a mutation in said nucleic acid allowing the classification of said SCID as radiosensible SCID.

The mutations that are searched comprise point mutations that lead to a non-conservative change in an amino-acid of the protein or production of a premature termination codon, deletions, insertions, or modifications due to changes in the genomic DNA corresponding to SEQ ID No 1, and the splice donor and acceptors sites flanking the exons.

The invention is also drawn to a method of diagnosis in a patient, including a prenatal diagnosis, of a condition chosen in the group consisting of a SCID, a predisposition to cancer, a immune deficiency, and the carriage of a mutation increasing the risk of progeny to have such a disease, comprising the step of analyzing the nucleic acid chosen in the group consisting of SEQ ID No 1, nucleotides 39-2114, 60-2114, 39-1193, and 60-1193 of SEQ ID No 1 and/or the protein coded by said nucleic acid in said patient, a mutation in said nucleic acid and/or protein indicating a increased risk of having said condition.

It is also encompassed that the method of diagnosis according to the invention is performed such as to analyze one or the two alleles of the patient, looking for any mutations (point mutations, deletions, insertions, mutations leading to incomplete splicing . . . ) that will lead to the production of a non functional protein. Therefore, it has to be understood that the analysis of the nucleic acid chosen in the group consisting of SEQ ID No 1, nucleotides 39-2114, 60-2114, 39-1193, and 60-1193 of SEQ ID No 1 is performed directly or indirectly on the genomic DNA.

These methods of diagnosis are preferably performed in vitro, on DNA or RNA that have been obtained from cells harvested from the patient.

The methods of diagnosis according to the nvention may be performed on the genomic DNA isolated from the patient, for example by amplification of the exons, in particular with the pairs of primers SEQ ID No 5 to SEQ ID No 32, which are located in the introns of the Artemis gene, and allow the amplification of the exons and of the junctions intron-exons, which the inventors have shown as mutated in some RS-SCID patients. It is clear that any primer that would amplify the exons or allow the analysis of the exon-intron junction may be used in this embodiment of the method of diagnosis according to the invention.

One way of performing a method of diagnosis according to the invention would be to perform a PCR-SSCP, or to sequence the amplification product to determine the mutations in the Artemis gene.

The protein ARTEMIS (or SNM1C) coded by the nucleic acid of the invention is therefore involved in V(D)J recombination and/or DNA repair. Mutations in the nucleic acid leading to the expression of a non-functional protein, when occurring on both alleles in a patient, lead to a SCID condition in said patient. It is also foreseen that the properties of the protein ARTEMIS may be exploited in other fields, such as cancer therapy, as compounds that interact with the protein in a cancerous cell may help sensitizing said cell to an antitumoral agent, the action of which is to shred the DNA (radiation, chemical agent).

The invention is therefore drawn to a method of identification of a compound capable of binding to the nucleic acid or to the protein of the invention, comprising the steps of
a) contacting said nucleic acid or protein with a candidate compound, and
b) determining the binding between said candidate compound and said nucleic acid or protein.

The methods for assessing the binding of a compound to a nucleic acid or a protein are well known in the art, and are preferably performed in vitro. A method to achieve such a goal may be to link the nucleic acid or the protein to a solid support on which the compound to test is flown, and to check the recovery of the compound after passage on the support. By adjusting parameters, it is also possible to determine the binding affinity. The compounds may also be found by other methods including FRET, SPA . . . when the compounds and the nucleic acid or protein are labeled. The assay may also be performed on the cells containing the nucleic acid of the invention, for example on a vector according to the invention, and/or expressing the protein according to the invention. This also gives the information of the capacity of the compound to go through the membrane and penetrate within cells. These cells can be bacterial cells (search for antibiotic compounds binding to the β-lactamase fragment of the protein), or mammalian cells.

The invention is therefore also drawn to a compound identified by the above-described method, said compound binding to the nucleic acid or the protein of the invention.

Particularly preferred compounds are compounds that bind to the β-lactamase region of the protein of the invention (first 180 amino-acids of SEQ ID No 2) or the associated b-CASP domain (amino-acids 181-385 of SEQ ID No 2). Such compounds may have a chemical formula close to the formula I or IV of WO 00/63213, said formula and the corresponding part of the specification being incorporated herein by reference, WO 99/33850, WO 01/02411 or U.S. Pat. No. 6,150,350, the description of the compounds being incorporated herein by reference.

A compound identified by a method according to the invention may be a compound with a chemical backbone (chemical compound), a lipid, a carbohydrate (sugar), a protein, a peptide, an hybrid compound protein-lipid, protein-carbohydrate, peptide-lipid, peptide-carbohydrate, a protein or a peptide on which has been branched different chemical residues.

The foreseen chemical compounds (with a chemical backbone), may contain one or more (up to 3 or 4) cycles, especially aromatic cycles, in particular having from 3 to 8 atoms of carbon, and having all kinds of branched groups (in particular lower alky, i.e. having from 1 to 6 atoms of carbon, keto groups, alcohol groups, halogen groups . . . ). The person skilled in the art knows how to prepare different variants of a compound starting from a given backbone by grafting these radicals on said backbone.

The method of the invention also allows the screening, detection and/or identification of compounds able to inhibit the biological activity of the ARTEMIS protein. Indeed, it is possible to test the compounds binding to the nucleic acid or the protein identified by the method according to the invention on an assay such as a complementation assay wherein a vector carrying SEQ ID No 1 or nucleotides 39-2114 of SEQ ID No 1 and expressing a functional protein is introduced in a cell harvested from a patient suffering from RS-SCID, and the compound is tested on its ability to inhibit the restoration of V(D)J recombination and/or DNA repair in said cells. The examples illustrate such an assay that is preferably performed in vitro.

The present invention thus allows the detection, identification and/or screening of compounds that may be useful for the treatment of diseases where V(D)J recombination and/or DNA repair is involved. Nevertheless, the compounds identified by the method according to the invention, in order to be used in a therapeutic treatment, may need to be optimized, in order to have a superior activity and/or a lesser toxicity.

Indeed, the development of new drugs is often performed on the following basis:
  screening of compounds with the sought activity, on a relevant model, by an appropriate method,
  selection of the compounds that have the required properties from the first screening test (here, modulation of V(D)J recombination and/or DNA repair),
  determination of the structure (in particular the sequence (if possible the tertiary sequence) if they are peptides, proteins or nucleic acids, formula and backbone if they are chemical compounds) of the selected compounds,
  optimization of the selected compounds, by modification of the structure (for example, by changing the stereochemical conformation (for example passage of the amino acids in a peptide from L to D), addition of substituants on the peptidic or chemical backbones, in particular by grafting groups or radicals on the backbone, modification of the peptides (se in particular Gante "Peptidomimetics", in Angewandte Chemie-International Edition Engl. 1994, 33.1699-1720),
  passage and screening of the "optimized" compounds on appropriate models that are often models nearer to the studied pathology. At this stage, one would often use animal models, in particular rodents (rats or mice) or dogs or non-human primates, that are good the models of SCID or cancers, and to look for the phenotypic changes in said models after administration of the compound.

The present invention also encompasses the compounds that have been optimized after following the steps or equivalent steps as described.

The present invention is also drawn to one of the nucleic acid, the vector, the host cell, the protein, the antibody, and the compound of the invention as a medicament. These entities can indeed be used alone for the treatment of different types of diseases, in particular the ones in which V(D)J recombination and/or DNA repair is involved, said diseases including, without limitation, RS-SCID, immune deficiency, cancer. These entities can also be used in combination with another treatment that is appropriate for the disease, the use being simultaneous, separate or sequential.

In particular, the products according to the invention may be used in combination with cytokines, growth factors, antibiotics, anti-inflammatories, and/or chemotherapeutic agents as is appropriate for the indication being treated.

The invention is also drawn to a pharmaceutical composition comprising a pharmaceutically acceptable excipient, carrier or diluent with at least one of the nucleic acid, the vector, the host cell, the protein, the antibody, and the compound of the invention.

The person skilled in the art knows the appropriate excipients and carriers that can be used, and one may cite, as ways of example, water for injection, preferably supplemented with other materials common in solutions for administration to mammals, or neutral buffered saline or saline mixed with serum albumin. Some carriers may be found in Remington's Pharmaceutical Sciences, 18th Edition, A. R. Gennaro, ed., Mack Publishing Company [1990].

The pharmaceutical composition of the invention may be administrated orally, nasally, mucosally, or injected in particular intravenously, intramuscularly, or subcutaneously. The carrier and/or excipient will be chosen appropriately depending on the way of administration. U.S. Pat. No. 6,165,753 already cited gives examples of suitable routes of administration and excipients (column 17 line 31 to column 21 line 55, the general information being incorporated herein by reference).

The invention is also directed to a method for the therapy of a severe combined immunodeficiency (SCID), comprising administering to a subject at least one of the nucleic acid, the vector, the host cell, the protein, the antibody, the compound and the pharmaceutical composition of the invention.

U.S. Pat. No. 6,165,753 also describes methods of gene therapy, and this teaching is incorporated by reference.

In a preferred embodiment, said nucleic acid is administered to said subject such as to enter stem cells, that is the cells that are the genitors of the cells of the immune system. This may be performed in vivo, or ex vivo, after harvesting the cells of the patient, selecting the stem cells, introducing the nucleic acid within said selected cells, and reinjecting the transformed cells to the patient.

For penetration of the nucleic acid within the cells, different means may be used by the person skilled in the art. In particular, it is possible to introduce said nucleic acid within the cells by means of a viral vector.

Said virus may be of human or of non-human origin, as long as it possesses the capability to infect the cells of the patient. In particular, said virus is chosen from the group consisting of adenoviridiae, retroviridiae (oncovirinae such as RSV, spumavirinae, lentivirus), poxyiridiae, herpesviridiae (HSV, EBV, CMV . . . ), iridiovirus, hepadnavirus (hepatitis B virus), papoviridiae (SV40, papillomavirus), parvoviridiae (adeno-associated virus . . . ), reoviridiae (reovirus, rotavirus), togaviridiae (arbovirus, alphavirus, flavivirus, rubivirus, pestivirus), coronaviriadiae, paramyxoviridae, orthomixoviridae, rhabdoviridae (rabies virus), bunyaviridae, arenaviridae, picornaviridae (enterovirus, Coxsackievirus, echovirus, rhinovirus, aphtovirus, cardiovirus, hepatitis A virus . . . ), Modified Virus Ankara, and derived viruses thereof.

By derived viruses, it is intended to mean that the virus possesses modifications that adapt it to the human being (if it is a virus from a non-human origin that could not infect human cells without said modifications), and/or that reduce its potential or actual pathogenicity. In particular, it is best if the virus used for the gene transfer is defective for replication within the human body. This is an important safety concern, as the control of the expression of the functional gene may be a concern for the implementation of the method of the invention. One does not either whish to have a dissemination to other cells or to other people of the viral vector carrying the gene of therapeutic interest.

This is why the viral vector used in the method of the invention is preferably deficient for replication, and would therefore be prepared with the help of a auxiliary virus or in a complementary cell line, that would bring in trans the genetic material needed for the preparation of a sufficient viral titer.

Such defective viruses and appropriate cell lines are described in the art, for example in U.S. Pat. No. 6,133,028 that describes deficient adeno-associated viruses (AAV) and the associated complementation cell lines, and the content of which is herein incorporated by reference. Other suitable viruses are described for example in WO 00/34497. For adenoviruses or AAV, it may be interesting to delete the E1 and/or E4 regions.

For the MFG virus described below, one can use the complementation Ψ-CRIP cell line that was described in Hacein-Bey et al. (1996, Blood. 87, 3108-16), incorporated herein by reference. Other appropriate cell lines could also be used.

In order to improve the long lasting effect of the correction, one would prefer a virus that allows the integration of said functional gene into a chromosome of the infected cells.

In particular, one would chose adenoviruses, some of which defective for replication are well know by the person skilled in the art, or retroviruses, in particular murine derived retroviruses. Among the retroviruses that can be used, one would prefer a myeloproliferative sarcoma virus (MPSV)-based vector as described in Bunting et al. (1998, Nature Medecine, 4, 58-64, the content of which is incorporated herein by reference). Another well suited retrovirus that can be used for the implementation of the method of the invention is the MFG vector, derived from the MLV virus (Moloney retrovirus), described in Hacein-Bey et al. (1996, Blood. 87, 3108-16) or Cavazzana-Calvo et al. (2000, Science, 288, 669-72), the content of both these documents being incorporated herein by reference.

The choice of the virus to be used for the implementation of the method of the invention will be function of the characteristics of said virus and of the complementation cell line. It is clear that different viruses have different properties (in particular LTR in retroviruses), and that the viruses and cell lines cited above are only examples of means that can be used for the implementation of the method of the invention, and that they shall not be considered as restrictive. The person skilled in the art knows how to choose the best combination gene-virus-cell line and/or auxiliary virus for any given situation.

In another embodiment, said nucleic acid is introduced within cells by means of a synthetic vector which can be chosen from the group consisting of a cationic amphiphile, a cationic lipid, a cationic or neutral polymer, a protic polar compound such as propylene glycol, polyethylene glycol, glycerol, ethano, 1-methyl-L-2-pyrrolidone or their derivatives, and an aprotic polar compound such as dimethyl sulfoxide (DMSO), diethyl sulfoxide, di-n-propyl sulfoxide, dimethyl sulfone, sulfolane, dimethylformamide, dimethylacetamide, tetramethylurea, acetonitrile or their derivatives. The person skilled in the art is aware of synthetic vectors that can be used and allow a high level of transfection, such as Lifofectine and Lipofectamine reagents available from Life Technologies (Bethesda, Md.).

It is envisioned that the expression of the functional Artemis gene within the cells of the SCID patient will bring a selective advantage to said cells or progeny of said cells, as compared to non-transformed cells or progeny of said non-transformed cells, and lead to a improvement in the condition of the patient.

As selective advantage, it is understood that the proportion of cells that have been corrected by introduction of the functional gene compared to the cells of the same type in which said gene is not functional will increase, and that it would lead to a alleviation of the disease, or even a cure.

The possibility to obtain such a selective advantage has been demonstrated for another gene by Cavazzana-Calvo et al. (2000, Science, 288, 669-72).

The method of the invention is best performed when the cells within which is introduced the functional Artemis gene are stem cells or undifferentiated cells that are progenitors of the cells lacking expression of the functional Artemis gene. This would lead to the fact that a large number of cells are corrected within time, as the progeny of said stem cells would also be corrected. Furthermore, as the stem cells would differentiate over time to a large number of cells, there is only the need to transfect a small initial number of cells.

It is possible to identify some of the stem cells for the haematopoietic system, as they harbor the marker CD34 at their surface (CD34+ cells). Their targeting may be performed in vivo, or ex vivo (sorting of these cells, transfection and reinfusion by intravenous injection). The person skilled in the art knows that stem cells can be isolated from cord blood.

It may be interesting to induce the cell cycle of said stem cells, in order to increase the efficiency of transfection. This is particularly true when the method of the invention is performed on cells ex vivo.

Indeed, some of the vectors that can be used for the entry of the gene of interest in the cells are vectors that can only be incorporated in non-quiescent cells. In order to have the cells replicate, one will preferably use growth factors and/or cytokines, such as CSF (GM-CSF, M-CSF, G-CSF), interleukines (preferably IL-1, 2, 3, 4, 6, 7, 8, 9, 10, 15), interferons (in particular α or γ). One could also use stem cell factor, megakaryocyte differentiation factor, optionally coupled with polyethylene-glycol, or Flt-3-L. These factors may be use alone or in combination.

When the method of the invention is performed ex vivo, the stem cells may also be maintained in a medium complemented with other nutriments such as serum (fetal bovine serum, as usual, or preferably fetal cell serum). It may also be interesting to maintain the cells to be transfected in plates containing cell adhesion elements such as cell adhesion proteins (in particular fibronectin, or vitronectin) or the peptides that have been shown to promote cell adhesion. It is clear that the choice of the culture medium will be influenced by the type of cells and the sought-after goal.

The invention is also drawn to a method for the therapy of cancer in a patient, comprising administering to said patient at least one of the nucleic acid, the vector, the host cell, the protein, the antibody, the compound and the pharmaceutical composition of the invention, preferably in addition with a genotoxic agent, the use being simultaneous, separate or sequential.

The invention also relates to methods of modulation of the expression and/or activity of the protein ARTEMIS in a cell, comprising contacting said cell with at least a compound selected in the group consisting of the nucleic acid, the vector, the host cell, the protein, the antibody, the compound and the pharmaceutical composition of the invention. This modulation may be performed in vitro, but also in vivo, in any mammal, the compound being appropriately formulated. Interesting compounds include the compounds of the invention that bind to the β-lactamase or the β-CASP fragment of the protein, but also compounds that have an antisense activity.

Antisenses specifically bind to the cDNA and interfere with the translation of the protein, possibly by inducing the digestion of said cDNA by RNase H. The antisenses envisioned in the present invention may be modified and may harbor phosphorothioates, or methylphosphonates bonds. They may also be capped at one extremity, in order to reduce their degradation by nucleases.

As the protein ARTEMIS harbors a β-lactamase fragment, the invention also encompasses a method of biotherapy in a patient comprising administering to said patient at least one of the nucleic acid, the vector, the host cell, the protein, the antibody, the compound and the pharmaceutical composition of the invention. It is particularly preferred to use the compound of the invention that binds to the β-lactamase part of the ARTEMIS protein.

Another object of the invention is the use of at least one of the nucleic acid, the vector, the host cell, the protein, the antibody, the compound and the pharmaceutical composition of the invention for the preparation of a medicament intended for the treatment of a disease where V(D)J recombination and/or DNA repair is involved, said disease being in particular chosen in the group consisting of cancer, SCID, especially RS-SCID, immune deficiency, for example due to problems in the switch of the heavy chains of the immunoglobulins, or due to problems in the process of somatic hypermutation of the immunoglobulins.

The invention also relates to a transgenic non-human mammal having integrated into its genome the nucleic acid sequence of the invention, especially a nucleic acid sequence chosen in the group consisting of nucleotides 39-2114, 60-2114, 39-1193 and 60-1193 of SEQ ID No 1, operatively linked to regulatory elements, wherein expression of said coding sequence increases the level of the ARTEMIS protein and/or the level of V(D)J recombination and/or DNA repair of said mammal relative to a non-transgenic mammal of the same species.

It is preferred when the nucleic acid sequence that is integrated in the genome of the transgenic animal codes for a polypeptide chosen in the group of polypeptides comprising amino-acids 1-692, 8-692, 1-385 or 8-385 of SEQ ID No 2. of SEQ ID No 2. It is also preferred when the nucleic acid sequence that is integrated in the genome of the transgenic animal codes for a polypeptide chosen in the group of polypeptides consisting of amino-acids 1-692, 8-692, 1-385 or 8-385 of SEQ ID No 2.

It is also envisioned that the regulatory elements (promoters, enhancers, introns, similar to those that can be used in mammalian expression vectors) may be tissue-specific, which allows over-expression of the ARTEMIS protein only in a specific type of cells. In particular, the person skilled in the art is aware of the different promoters that can be used for this purpose.

The insertion of the construct in the genome of the transgenic animal of the invention may be performed by methods well known by the artisan in the art, and can be either random or targeted. In a few words, the person skilled in the art will construct a vector containing the sequence to insert within the genome, and a selection marker (for example the gene coding for the protein that gives resistance to neomycine), and may have it enter in the Embryonic Stem (ES) cells of an animal. The cells are then selected with the selection marker, and incorporated into an embryo, for example by microinjection into a blastocyst, that can be harvested by perfusing the uterus of pregnant females. Reimplantation of the embryo and selection of the transformed animals, followed by potential backcrossing allow to obtain such transgenic animal. To ibtain a "cleaner" animal, the selection marker gene may be excised by use of a site-specific recombinase, if flanked by the correct sequences.

The invention also relates to a transgenic non-human mammal whose genome comprises a disruption of the endogenous ARTEMIS gene, wherein said disruption comprises the insertion of a selectable marker sequence, and wherein said disruption results in said non-human mammal exhibiting a defect in V(D)J recombination and/or DNA repair as compared to a wild-type non-human mammal.

In a preferred embodiment, said disruption is a homozygous disruption.

In a preferred embodiment, said homozygous disruption results in a null mutation of the endogenous gene encoding ARTEMIS.

In a preferred embodiment, said mammal is a rodent, in the most preferred embodiment, said rodent is a mouse.

The invention also encompasses an isolated nucleic acid comprising an ARTEMIS knockout construct comprising a selectable marker sequence flanked by DNA sequences homologous to the endogenous ARTEMIS gene, wherein when said construct is introduced into a non-human mammal or an ancestor of said non-human mammal at an embryonic stage, said selectable marker sequence disrupts the endogenous ARTEMIS gene in the genome of said non-human mammal such that said non-human mammal exhibits a defect in V(D)J recombination and/or DNA repair as compared to a wild type non-human mammal.

Said construct is used to obtain the animals that have the disrupted copy of the Artemis gene, and are generally carried on a vector that is also an object of the invention.

The invention also relates to a mammalian host cell whose genome comprises a disruption of the endogenous Artemis gene, wherein said disruption comprises the insertion of a selectable marker sequence. Preferably, said disruption is homozygous and leads to a non-expression of a functional ARTEMIS protein (or expression of a non-functional protein).

It is to be noted that the disruption may be obtained by methods known in the art and may be conditional, i.e. only present in specific types of cells, or induced at some moments of the development. The method to achieve such a goal may be to use site specific recombinases such as Cre (recognizing lox sites) or FLP (recognizing FRT sites) recombinases, under the control of cell-specific promoters. These recombinases (especially Cre) have been shown to be suitable for modifications and their activity may be induced by injection of a substrate (such as an hormone). These modifications are known in the art and may be found, for example in Shibata, et al. (1997, Science 278, 120-3).

Therefore, the transgenic animal or the cell of the invention may not show anymore the selectable marker, which may have been removed upon action of the recombinases, that lead to the disruption of the gene. Nevertheless, in the process of obtaining such disruption, a selectable marker has been inserted within the Artemis gene, mostly to allow selection of the transformed cells.

U.S. Pat. No. 6,087,555 describes one way of obtaining a knock-out mouse, and the general teaching of this patent is incorporated herein by reference (column 5, line 54 to column 10 line 13). In this patent, it is described an OPG knock-out mouse, but the same method applies to an ARTEMIS knock-out mouse. The person skilled in the art will also find information in Hogan et al. (Manipulating the Mouse Embryo: a Laboratory Manual, Cold Spring Harbor Laboratory Press, Cold Spring Harbor, N.Y.; 1986).

In another embodiment, the invention relates to a non human transgenic mammal whose genome comprises a first disruption that is of the endogenous ARTEMIS gene, and a second disruption that is of the endogenous p53 gene. In the preferred embodiment, at least said first disruption or said second disruption is an homozygous disruption. In the most preferred embodiment, said first disruption and said second disruption are both homozygous disruptions, which result in particular in null inactivation of both ARTEMIS and p53 genes.

In the preferred embodiment, the transgenic mammal is a rodent, preferably a rat or a mouse.

This transgenic mammal may be used as a model for studying pro-B cell lymphomas. Indeed, the invention relates to a method for providing a model for studying pro-B cell lymphomas, comprising providing said transgenic mammal to a person in need of such model for studying pro-B cell lymphomas, and to a method for studying pro-B cell lymphomas, comprising studying said transgenic mammal.

The animals and "knock-out" cells of the invention may also be used for identification of pharmacologically interesting compounds. Therefore, the invention also relates to a method of screening compounds that modulate V(D)J recombination and/or DNA repair comprising contacting a compound with the non-human mammal or the knock-out host cell of the invention, and determining the increase or decrease of V(D)J recombination and/or DNA repair into said non-human mammal or said host cell as compared to the V(D)J recombination and/or DNA repair of said non-human mammal or said host cell prior to the administration of the compound.

A method of testing the genotoxicity of compounds comprising contacting a compound with the non-human mammal or a host cell of the invention, and determining the increase or decrease of V(D)J recombination and/or DNA repair into said non-human mammal or said host cell as compared to the V(D)J recombination and/or DNA repair of said non-human mammal or said host cell prior to the administration of the compound, is also object of the invention.

The present invention also relates to the determination of the binding partners of the proteins coded by one of the nucleic acid of the invention by using the double hybrid assay, for example the assay described by Finley and Brent (*Interaction trap cloning with yeast,* 169-203, in DNA Cloning, Expression Systems: a practical Approach, 1995, Oxford Universal Press, Oxford, the content of which is incorporated herein by reference).

Basically, a yeast strain is transformed by two plasmids encoding either the bait protein (the protein coded by one of the nucleic acid of the invention) or the protein supposed to be a binding partner of the bait protein (the prey protein).

Upon binding of the 2 proteins, a reporting gene is induced and the yeast becomes able to metabolize a substrate in the medium. It is thus possible to determine the binding between two proteins. It is very quick to use a cDNA library in order to screen multiple preys at the same time.

The double hybrid assay is not limited to yeast, but may also be performed in other types of cells, such as mammal cells or bacterial cells.

The invention also relates to the complexes that are made of a protein coded by one of the nucleic acid of the invention and one of its binding partners.

Function of Artemis

Although it can inferred from the phenotype of RS-SCID patients that Artemis is part of the ubiquitous machinery involved in DNA dsb repair that is shared by the V(D)J recombination process, the precise function for this new factor remains to be defined.

The repeated search for a global homolog of Artemis in other species in protein databases failed to provide a strong candidate. The only similarity comes from the 0083 peptide, which includes the whole N-terminus moiety of Artemis, to the various members of the SNM1 family.

However, Artemis is clearly not the human ortholog of either murine SNM1 or yeast PSO2 for at least two reasons:
  First, despite their SNM1 similarity regions, the three proteins differ in their associated domains. In particular, the 331 amino acids composing the C-terminal region of Artemis are not present in SNM1/PSO$_2$ and do not show any obvious similarities with any other known protein.
  Secondly, while murine and yeast SNM1/PSO$_2$ mutants demonstrate a strong defect in the repair of DNA damages caused by DNA interstrand cross-linking agents (Henriques and Moustacchi, 1980; Dronkert et al., 2000), they do not display elevated sensitivity to ionizing radiations, indicating that these two proteins are probably not directly involved in the repair of DNA dsb.

This is in sharp contrast to the phenotype of RS-SCID patients whose primary molecular defect is indeed the absence of DNA dsb repair, illustrated by the lack of coding joint formation in the course of V(D)J recombination and the increased sensitivity of bone marrow and fibroblast cells to γ rays (Cavazzana-Calvo et al., 1993; Nicolas et al., 1998).

Interestingly, Artemis, murine SNM1 and yeast PSO$_2$ share a domain adopting a metallo-β-lactamase fold (Aravind, 1997) and probably its associated enzymatic activity, given the presence of nearly all the critical catalytic residues (or conserved residues which could substitute them for function). However, there is no obvious consensus with regard to the nature of the various metallo-β-lactamase substrates, outside of a general negatively charged composition. Sequence analysis revealed the existence of a conserved region that accompanies the metallo-β-lactamase domain in members of the Artemis/SNM1/PSO$_2$ subfamily (data not shown), including various other sequences related to nucleic acid metabolism such as two subunits of the cleavage and polyadenylation specificity factor (CPSF).

It is proposed to name this domain, which will be described in detail elsewhere, βCASP for metallo-β-lactamase associated CPSF Artemis SNM1/PSO$_2$ domain. This domain, although highly divergent and tolerating multiple insertions (e.g. within yeast PSO$_2$), harbors several conserved residues, such as the H319 in Artemis, which could play a role in the reaction catalyzed by members of this subfamily.

It is tempting to speculate that this domain could contribute to substrate binding, in a similar way as the α-helical domain of glyoxalase, another member of the β-lactamase family (Cameron et al., 1999).

Artemis in the NHEJ Pathway of DNA Repair

DNA dsb can be repaired by either homologous recombination (HR) or by the non-homologous end-joining pathway (NHEJ)(review in (Haber, 2000)). While HR is the predominant repair pathway in yeast, NHEJ is mostly utilized in higher eukaryotes and represents the DNA repair pathway followed during V(D)J recombination.

At least three protein complexes are thought to act in concert or sequentially at the site of the RAG1/2 derived dsb. The Ku70-80 complex is probably recruited first at the site of the lesion, followed by the addition of the DNA-PKcs subunit. This initial complex is considered as the primary DNA damage sensor that will activate the DNA repair machinery. The XRCC4/DNA-LigaseIV represents the best candidate to actually repair the gap. More recently, the RAD50/E11/NBS1 complex which was known to participate in NHEJ (Carney et al., 1998; Varon et al., 1998) was found at the site of the rearranging TCR genes, arguing for its possible involvement in the DNA repair phase of the V(D)J recombination (Chen et al., 2000).

One would like to know of course how Artemis plays its role in this cascade. At this point only speculative answers based upon the analogy of phenotypes between the various deficient models including the RS-SCID can be provided. It is most unlikely that Artemis be linked to the RAD50/MRE11/NBS1 complex. Indeed, in both Nijmegen and ataxia-telangectasia-like disorder (ATLD) patients, mutations in the NBS1 and the MRE11 genes lead to chromosomal instability accompanied by a profound defect in DNA damage induced G1 arrest of the cell cycle (G0/G1 checkpoint) while V(D)J recombination is spared (Carney et al., 1998; Varon et al., 1998). This is in sharp contrast to the normal G1 arrest in RS-SCID fibroblasts following irradiation (unpublished results).

Concerning the XRCC4/DNA-ligaseIV complex, two major differences exist between the RS-SCID condition and the XRCC4 and DNA-LigaseIV KO mice:

First, a complete null allele of Artemis (such as in P6, P15, and P40) does not lead to embryonic lethality in humans. This observation does not support an implication of Artemis in this phase of NHEJ.

Second, the rejoining of linearized DNA constructs introduced in RS-SCID fibroblasts is normal (unpublished results) while this assay, when defective, is highly diagnostic of abnormal NHEJ in yeast (Teo and Jackson, 1997; Wilson et al., 1997).

Perhaps the most evident link between Artemis and NHEJ is found in regard to the Ku/DNA-PK complex. Indeed, human RS-SCID patients and scid mice, which harbor a mutation in the DNA-PKcs encoding gene, are the only two known conditions where a V(D)J recombination associated DNA repair defect affects uniquely the formation of the coding joints.

The signal joint formation is also affected in the context of a defective V(D)J recombination in all the other analyzed settings.

Moreover, the manifestations of the DNA repair defect seem pretty much restricted to the immune system in both human RS-SCID patients and scid mice and do not seem to lead to neurologic disorders or development of cancer for example, two manifestations that are often associated with defects in the other players of the NHEJ Roth and Gellert, 2000).

In conclusion, the invention describes the identification and cloning of the gene coding for Artemis, a novel actor of the V(D)J recombination. Mutations of Artemis are causing T-B-SCID defects in humans owing to an absence of repair of the RAG1/2-mediated DNA double strand break. Artemis belongs to a large family of molecules that adopted the metallo-β-lactamase fold as part of their putative catalytic site. One branch of this family, which also includes yeast SNM1 and murine PSO2, has appended another domain, which is named βCASP, that may target the activity of this subgroup of proteins towards nucleic acids and thus, serves the purpose of DNA repair.

Finally, other domains, yet to be defined, are probably responsible for directing the various Artemis/SNM1/PSO2 proteins to their specific DNA repair pathways; the dsb repair for Artemis or the DNA-ICL repair for SNM1/PSO$_2$.

The following examples are intended for illustration purposes only, and should not be construed as limiting the scope of the invention in any way

EXAMPLES

Example 1

Cloning of the Artemis cDNA

Patients and Cells

13 RS-SCID patients from 11 families were analyzed in this study having been selected for their typical phenotype of autosomal recessive SCID with complete absence of peripheral T and B lymphocytes, but presence of natural killer cells (Fischer et al., 1997). All the patients showed an impaired V(D)J recombination assay in fibroblasts, and for all RS-SCID families except P16, P40 and P47 radiosensitivity status could be determined on bone marrow cells and/or fibroblasts ((Cavazzana-Calvo et al., 1993; Nicolas et al., 1998; Moshous et al., 2000) and our unpublished results). Genotyping of the consanguineous families using polymorphic microsatellite markers as reported elsewhere (Moshous et al., 2000) concurred in every case with our previously described localization of RS-SCID on chromosome 10p. The study was based on four patients of French origin (P1, P3, P6 and P15), one of which (P15) was born to related parents, one was of Italian origin (P16), one Greek (P4) and one African (p2). The remaining patients originate from four consanguineous Turkish families, two of them being related (P38, P5, P11 and P12 respectively). Informed consent was obtained from the families prior to this study. Primary fibroblast cell lines were derived from skin biopsies and pseudo-immortalized with SV40 as described elsewhere (Nicolas et al., 1998) and cultured in RPMI 1640 (GIBCO BRL) supplemented with 15% fetal calf serum.

Artemis cDNA Cloning and Genomic Amplification

First strand cDNA was synthesized from fibroblast RNA. Artemis full-length coding sequence was amplified by polymerase chain reaction (PCR) on cDNA using the Advantage-GC cDNA PCR Kit (Clontech) according to the manufacturers' recommendations and 0083F1 (5'-GATCGGCGGCGCTATGAGTT-3', SEQ ID No 3) and 169F (5'-TGTCATCTCTGTGCAGGTTT-3', SEQ ID No 4) primers designed from the AA278590 and AI859962 EST sequences. The PCR products were sequenced directly on an ABI377 sequencer (Perkin-Elmer) using BigDyeTerminator Cycle Sequencing Ready Reaction (Applied Biosystems) with a series of internal oligonucleotides. Because of several alternatively spliced transcripts, sequencing was also performed on cloned PCR products. Artemis full-length cDNA was subcloned into pIRES-EGFP (Clontech) for subsequent use in transfection experiments. Genomic structure of the Artemis gene was deduced by alignment of the cDNA sequence to the draft sequence of the Bac 2K17 (AL360083). Series of oligonucleotide primer pairs were designed for the specific amplification of each exon. Exon 4 and exon 5 PCR products were cloned into pGemT (Promega) for subsequent use in Southern blot analysis (see below).

The primers that were used for genomic amplification of the different exons 1 to 14 correspond to SEQ ID No 5 to SEQ ID No 32. These pairs of primers allow the amplification of each exon, as indicated in the sequence listing, the number of the exon being after "Ex", "F" meaning Forward and "R" Reverse.

Results

As part of its effort in sequencing the human chromosome 10, the "Chromosome 10 Mapping Group" at the Sanger Center constructed several bacterial artificial chromosomes (BACs) contigs covering the entire chromosome 10 (http://www.sanger.ac.uk/HGP/Chr10). Two of these contigs, 10ctg1105 and 10ctg23 (FIG. 1A), were of particular interest as they included several BACs bearing the RS-SCID region flanking markers D10S1664 and D10S674, as well as D10S191 and D10S1653, that showed the maximum pairwise LOD scores in A-SCID populations (Li et al., 1998).

A systematic survey of the nucleotide sequences, covering the 24 BACs present in the two contigs, released by the "Human Chromosome 10 Sequencing Group" at the Sanger Center (http://webace.sanger.ac.uk/cgi-bin/ace/simple/10ace) was initiated. The analyses were based on in silico nucleotide sequence annotation with GENESCAN (3urge and Karlin, 1997) (http://bioweb.pasteur.fr/seqanal/interfaces/genscan.htnl) and FGENESH (Salamov and Solovyev, 2000) (http://genomic.sanger.ac.uk/gf/gfb.htrnl) softwares, two programs aimed at searching for putative peptide encoding genes in large genomic DNA sequences. All predicted peptides were subsequently run against the translated nonredundant GENBANK/EMBL nucleotide databases using TBLASTN. On the release of the AL360083 draft sequence, originated from the 2K17 BAC, FGENESH predicted a 149 amino-acids (aa) long peptide (subsequently named "0083" peptide) within which 121 aa turned out to be 35% and 31% identical to the MuSNM1 (AAF64472) and Yeast PSO2 (P30620) proteins respectively. The same peptide prediction was obtained using GENESCAN.

SNM1 and PSO2 are two proteins involved in the reparation of DNA damages caused by DNA interstrand cross-linking agents (ICL) including cisplatin, mitomycin C, or cyclophosphamide ((Henriques and Moustacchi, 1980; Dronkert et al., 2000) and references therein). Mouse and yeast mutants for SNM1/PSO$_2$ are hypersensitive to several agents that cause ICLs but not to γ-rays in contrast to RS-SCID patients in whom hypersensitivity to γ-rays was found in both bone marrow cells and fibroblasts. The putative "0083" peptide encoding gene represented a good candidate owing to its chromosomal localization and the similarity of the "0083" peptide with DNA-repair proteins, despite the important discrepancy in the radiosensitivity phenotype. The validity of the putative "0083" peptide was established by searching for RNA transcripts encoding this peptide in the TIGR human Gene Indices database using TBLASTN (http://www.tigr.org/docs/tigrscripts/nhgi_scripts/tgi_blast.pl?organism=Human).

This query returned the THC535641 index within which the AA278590 represented the most 5' sequence and corresponded to the I.MA.G.E. clone 703546. The nucleotide sequence of this clone's opposite end (AA278850) matched the THC483503 index. The AI859962 nucleotide sequence in this second index provided the most 3' extension of the cDNA coding for the "0083" peptide. A complete cDNA was obtained by RT-PCR amplification of fibroblast RNA using 0083F1 and 169F primers chosen within the AA278590 and AI859962 nucleotide sequences respectively. This cDNA was directly sequenced and cloned into pGemT. Several clones represented non-productive transcripts generated by alternative splicing events (data not shown). The inventors concentrated on one set of clones that harbored the longest open reading frame. The entire cDNA sequence of 2354 bp (SEQ ID No 1) contains an open reading frame (ORF) of 2079 bp. The ATG at position 39 or the ATG at position 60 are assumed to represent the translational initiation site based on the analysis of surrounding nucleotides matching the Kozack consensus for translation initiation. The encoded protein of 692 or 685 aa, which was named Artemis (and corresponds to SNM1C), has a predicted molecular weight of about 78 kD. The "0083" peptide (corresponding to the peptide coded by nucleotides 348 to 800 of SEQ ID No 1) corresponds to I106H254 (start at nucl. 39) and is part of a larger region that shows similarity to scPSO$_2$ and muSNM1.

It is not possible to fully ascertain that this cDNA represents the full-length sequence although repeated attempts to further extend the 5' sequence failed. The polyA tail in the 3' untranslated region of the sequence SEQ ID No 1 is encoded by the genomic sequence and is not the consequence of RNA processing, suggesting that this cDNA may extend further downstream. Functional complementation studies (see below) strongly suggest, however, that the full Artemis ORF has indeed been cloned. The Artemis gene structure (Table 1) was deduced by comparison of the cDNA sequence to the genomic (AL360083) sequence. Artemis is composed of 14 exons with sizes ranging from 52 bp to 1160 bp. Four alternative exons were identified in various Artemis cDNA clones and result in non-productive splicings (data not shown).

TABLE 1 exon boundaries of the ARTEMIS gene

| | Length | Splice acceptor | Coding Sequence | | Splice donor |
|---|---|---|---|---|---|
| Exon 1 | 147 bp | | GCGGTT... | ...ACAAAG | Gtgagt |
| Exon 2 | 52 bp | ttttag | ATCACA... | ...GTGCAG | gtaatt |

TABLE 1-continued exon boundaries of the ARTEMIS gene

| | Length | Splice acceptor | Coding | Sequence | Splice donor |
|---|---|---|---|---|---|
| Exon 3 | 85 bp | tttcag | CTTGAA... | ...CGAATT | gtaagt |
| Exon 4 | 60 bp | ttacag | ATATCT... | ...GGAGAG | gtaact |
| Exon 5 | 56 bp | ttttag | AAGGAA... | ...AGTTAT | gtaagg |
| Exon 6 | 102 bp | tttcag | GTTTTT... | ...GGGCAG | gtactg |
| Exon 7 | 73 bp | tttcag | AGTCAA... | ...AGTCGG | gtaagt |
| Exon 8 | 141 bp | gtctag | GAGGAG... | ...GTCCAG | gtatgg |
| Exon 9 | 102 bp | ccttag | GTTCAT... | ...CCCAAG | gtacgt |
| Exon 10 | 137 bp | ttttag | GCAGAG... | ...TGTGAG | gtaaga |
| Exon 11 | 55 bp | ctttag | GACTGG... | ...AGTGAG | gtaaga |
| Exon 12 | 89 bp | ttctag | GTGAGA... | ...CGAAAT | gtgagt |
| Exon 13 | 95 bp | tttcag | ATTAAA... | ...ACTCAG | gtaaga |
| Exon 14 | 1160 bp | ccacag | AGGAGG... | ...AAAAAA | |

The RS-SCID had previously been assigned to a 6.5 cM chromosomal region flanked by the DIOS1664 and D10S674 polymorphic markers, a region too large for classical cDNA selection studies (Li et al., 1998; Moshous et al., 2000). In silico annotation of draft genomic sequences covering this region led the inventors to the identification of the Artemis gene.

Example 2

Expression of Artemis

Southern Blot Analysis

Ten µg of high molecular weight DNA were digested with HindIII or Eco88I, run onto 0.7% agarose gel, blotted on nylon membrane (Genescreen) under vacuum and hybridized with P32 labeled Artemis exon 5 and exon 4 specific probes.

RNA Expression Analysis

PCR-ready cDNA from several tissues were purchased from Clontech and amplified with Artemis specific primers 0083F4 (5'-AGCCAAAGTATAAACCACTG-3', SEQ ID No 33) and 169F (SEQ ID No 4) or manufacturer provided GAPDH primers as control and run onto 1% agarose gels. Artemis specific PCR products were blotted onto nylon membrane and hybridized with an internal $P^{32}$ labeled oligonucleotide, whereas the GAPDH PCR control was revealed by ethidium bromide staining.

Results

Increased radiosensitivity of RS-SCID to γ rays is not restricted to the cells of the immune system but is also a characteristic of fibroblasts, suggesting that Artemis is ubiquitously expressed. This was confirmed by PCR analysis on a panel of 15 cDNAs representing a wide range of hematopoietic and non-hematopoietic tissues.

The level of Artemis expression is ubiquitous but weak and required 30 PCR cycles (38 cycles for the skeletal muscle) to get an appropriate signal with an internal P32 labeled oligonucleotide, compared to the strong ethidium bromide staining obtained for the control gene GAPDH.

Low level expression of Artemis could reflect a general property of the SNM1 protein family as the basal expression of mSNM1 in ES cells was found very low as well (Dronkert et al., 2000). Of note, compared to other tissues, Artemis expression was not increased in thymus or bone marrow, the sites of V(D)J recombination.

As expected, given the generalized increased radiosensitivity in RS-SCID patients' cells (Cavazzana-Calvo et al., 1993), Artemis demonstrated a pleiotropic expression pattern.

Example 3

The Artemis Gene is Mutated in Human RS-SCIDs

Mutation Analysis

Artemis mutation sequence analyses were performed either on cDNA following RT-PCR amplification or on genomic DNA following exon-specific PCR amplification. All PCR products were directly sequenced using BigDyeTerminator Cycle Sequencing Ready Reaction.

Results

The structure and the sequence of the Artemis gene was analyzed in a series of 11 RS-SCID families including 13 patients (Table 2 and FIG. 1). Three patients (P6, P15, and P40) were characterized by a complete absence of the Artemis transcript caused by a genomic deletion extended from exon 1 to 4. This mutation can be considered as a complete null allele.

The same genomic deletion was present on one allele in P1 who carried a C279T nucleotide change on the other allele that led to the formation of a nonsense codon at R74. Homozygous C279T mutation was also present in P2 and found heterozygous in P4.

Two other genomic deletions were characteristic of this series of RS-SCID patients. A homozygous deletion spanning exons 5 to 8 in P47 led to the formation of a cDNA in which exon 4 was spliced in frame to exon 9, resulting in a putative protein lacking K96 to Q219. In P3, an heterozygous genomic deletion of exons 5 and 6 resulted in the out of frame splicing of exon 4 to 7 leading to a frameshift at K96. The second allele in this patient carried an heterozygous G to C nucleotide change in the exon 11 canonical splice donor sequence which caused the out of frame splicing of exon 10 to 12 leading to a frameshift at T300.

Lastly, three other splice donor sequence mutations were identified in six patients. A heterozygous G to A nucleotide change in the exon 10 splice donor site in P4 gave rise to the production of a cDNA where the fusion of exon 9 to 12 preserved the open reading frame and potentially led to the production of a protein lacking A261 to E317. Homozygous G to T mutation in the exon 5 donor site was found in the siblings P5, P11, and P12 as well as in P38, creating the out of frame splicing of exon 4 to 6 and the formation of a frameshift at K96. Although this form of cDNA lacking exon 5 as a result of alternative splicing event was also detected at low level in RNA from normal cells (data not shown), it accounted for all the cDNAs in P5 and P38. In patient P16, a homozygous deletion of G818 in exon 9, together with a homozygous C to T change nine nucleotides downstream in the intron caused the formation of a frameshift at A254.

Whenever samples of the patients' parents were available, they were tested for the presence of the mutations. This could confirm the inheritance of the mutations in P5, P11, and P12 as well as P38 and P16 by direct sequencing of the exon specific genomic PCR obtained from parents' DNA (data not shown) which concurs with the autosomal recessive inheritance.

In summary, all of the 13 RS-SCID patients tested in this series carry homozygous or heterozygous mutations in the Artemis gene. None of these mutations were simple missense, and one of them (genomic deletion of Exon 1 to 4) can be considered as a true null allele given the complete lack of Artemis transcript in P6, P15, and P40. All mutations are recapitulated in FIG. 1 and Table 2.

TABLE 2

Mutations of the artemis gene in RS-SCID patients

| Patients | Mutation | Effect | Status |
|---|---|---|---|
| P1 | Genomic deletion (Exons 1-4) | No RNA | Heteroz. |
|  | C279T | R74X* | Heteroz |
| P2 | C279T | R74X | Homoz. |
| P3 | Genomic deletion (Exons 5-6) | K96 frameshift | Heteroz. |
|  | Exon-11 splice donor (G->C) | T300 frameshift | Heteroz. |
| P4 | C279T | R74X | Heteroz. |
|  | Exon-10 splice donor (G->A) | Del A254-E317 | Heteroz |
| P5/P11/P12/P38 | Exon-5 splice donor (G->T) | K96 frameshift | Homoz. |
| P6/P15/P40 | Genomic deletion (Exons 1-4) | No RNA | Homoz. |
| P16 | del G818 | A254 frameshift | Homoz. |
| P47 | Genomic deletion (Exons 5-8) | Del K96-Q219 | Homoz. |

*Stop codon

The first indication that Artemis was indeed the gene involved in the RS-SCID came from the identification of mutations in several patients. Altogether, 8 different alterations of the gene were found in 11 families. Although some of the mutations were recurrent, it was not possible to draw any clear correlation with the geographical origins of the patients.

Several interesting features arise from the analysis of these mutations:

Firstly, three of the identified modifications involve genomic deletions spanning several exons, leading to frameshift and appearance of a premature termination in two cases and an in-frame deletion of 216 aa in one case. This indicates that the Artemis gene may represent a hot spot for gene deletion.

Secondly, none of the mutations consists in simple nucleotide substitutions generating amino-acid changes, and only one, the C279T transversion, creates a nonsense mutation. The other nucleotide changes affect splice donor sequences leading to either frameshifts in three cases or to in frame deletion of part of the protein in one case.

Thirdly, in three patients (P6, P15, and P40) the genomic deletion comprises exon 1 to 4 and results in a complete absence of Artemis encoded cDNA. This deletion, which can be considered as resulting in a null allele, therefore demonstrates that Artemis is not an essential protein for viability, in contrast to XRCC4 and DNA-Ligase-IV for example (Barnes et al., 1998; Frank et al., 1998; Gao et al., 1998), or that it is partly redundant.

This information is of particular interest in the setting of a murine knockout counterpart to the human RS-SCID condition. The implication of Artemis in the RS-SCID condition was unequivocally established by complementation of the V(D)J recombination defect in patients' fibroblasts upon transfection of a wt Artemis cDNA (next example).

Example 4

Artemis Complements the RS-SCID V(D)J Recombination Defect

V(D)J recombination Assay

V(D)J recombination assay was performed as previously described (Nicolas et al., 1998). Briefly, $5 \times 10^6$ exponentially growing SV40-transformed skin fibroblasts were electroporated in 400 μl of culture medium (RPMI1640, 10% FCS) with 6 μg of RAG-1 and 4.8 μg of RAG-2 encoding expression plasmid together with 2.5 μg of either pHRecCJ (coding joint) or pHRecSJ (signal joint) V(D)J extrachromosomal substrates. These plasmids carry a LacZ gene interrupted by a DNA stuffer flanked by V(D)J recombination signal sequences. Upon recombination, the stuffer DNA is excised and the LacZ gene reassembled, giving rise to blue bacteria colonies when plated onto Xgal/IPTG medium. pARTE-ires-EGFP (2.5 μg) was added for complementation analysis. Transfected constructs were recovered after 48 h, reintroduced into DH10B bacteria and plated on Xgal/IPTG containing plates. Percentage of recombination was determined by counting blue and white colonies and calculating the ratio. Blue colonies were randomly picked and the plasmid DNA sequenced to analyze the quality of the V(D)J junctions.

Results

The inventors previously demonstrated the absence of V(D)J recombination-derived coding joint formation in RS-SCID patients' fibroblasts upon transfection of RAG1 and RAG2 expression constructs together with extrachromosomal V(D)J recombination substrates specific for the analysis of the coding (pHRecCJ) joint (Nicolas et al., 1998). In contrast, signal joint formation was always found normal in RS-SCID fibroblasts ((Nicolas et al., 1998) and Table 3).

The Artemis gene was cloned in the mammalian expression vector pIres-EGFP and assessed its functional complementation activity in the V(D)J recombination assay in fibroblasts from 7 RS-SCID patients using the pHRecCJ substrate (Table 3). In all cases, bacterial blue colonies were recovered following transfections in the presence of wt Artemis, attesting for the RAG1/2 driven recombination of the substrate, while virtually no such colonies were obtained in the absence of exogenous wt Artemis.

The frequencies of recombination events ranged from $1.5 \times 10^{-3}$ to $2.9 \times 10^{-3}$, which agreed with the $3.2 \times 10^{-3}$ frequency obtained when using a control fibroblast cell line. Sequence analysis of the recovered pHRecCJ plasmids forming blue colonies in this assay in fibroblast lines from P1 and P40 demonstrated that the junctions were bona fide V(D)J coding joints with limited trimming of the coding ends similar to those obtained in control fibroblasts (not shown).

Altogether, these results indicate that the V(D)J recombination defect in RS-SCID is directly related to the described mutations in the Artemis gene and can be complemented by the introduction of a wt Artemis cDNA in the patients' fibroblasts. Although transient high level expression of Artemis did not seem to be toxic, stable transfectants could not be derived to analyze the complementation of the hypersensitivity to ionizing radiation. This could be due to a toxicity of long-term high level expression of wt Artemis in the transfected fibroblasts. An analogous cellular toxicity was previously described upon overexpression of other human or murine homologs of SNM1 in vitro and may be a characteristic of this family of proteins (Dronkert et al., 2000). This is also in agreement with the physiological low-level RNA expression of these genes (see above).

It is interesting to note that the protein consisting of the first 385 amino-acids of SEQ ID No 2 was also able to complement the V(D)J recombination defect in this assay.

TABLE 3

Complementation of V(D)J Coding-joint formation in RS-SCID fibroblasts transfected with wt Artemis

| Cell line | wt Artemis plasmid | Coding (pHRecCJ) | | | Signal (pHRecSJ) | | |
| --- | --- | --- | --- | --- | --- | --- | --- |
| | | Blue col. | Total | R* | Blue col. | Total | R# |
| Control | − | 50 | 42,000 | 3.5 | 27 | 10,840 | 2.5 |
| | + | 16 | 15,000 | 3.2 | | | |
| P1 | − | 0 | 34,800 | <0.03 | 34 | 45,600 | 0.7 |
| | + | 23 | 40,000 | 1.7 | | | |
| P4 | − | 2 | 36,300 | 0.16 | 336 | 98,200 | 3.4 |
| | + | 23 | 54,000 | 1.3 | | | |
| P5 | − | 0 | 21,400 | <0.05 | 17 | 3,000 | 5.7 |
| | + | 52 | 61,600 | 2.5 | | | |
| | + | 65 | 16,300 | 11.9 | | | |
| | + | 48 | 10,800 | 13.3 | | | |
| | + | 48 | 20,000 | 7.2 | | | |
| P15 | − | 2 | 11,160 | 0.53 | 192 | 30,000 | 6.4 |
| | + | 16 | 31,200 | 1.5 | | | |
| P16 | − | 0 | 13,000 | <0.08 | 51 | 33,200 | 1.5 |
| | + | 30 | 13,680 | 6.6 | | | |
| P40 | − | 0 | 40,250 | <0.02 | nd | nd | nd |
| | + | 90 | 160,000 | 1.7 | | | |
| | + | 65 | 58,800 | 3.3 | | | |
| | + | 100 | 42,840 | 7.0 | | | |
| | + | 76 | 29,736 | 7.6 | | | |
| P47 | − | 0 | 28,200 | <0.003 | 25 | 66,800 | 0.4 |
| | + | 48 | 50,000 | 2.9 | | | |

*R(coding joints) = 3 × (Blue col.)/(Total) × 1,000;
R(signal joints) = (Blue col.)/(Total) × 1,000

Example 5

Artemis Belongs to the metallo-β-lactamase Superfamily

Database searches using the BLAST2 program with the Artemis aa sequence as query revealed significant similarities to several proteins, including the yeast PSO2 and murine SNM1 proteins, over the first 360 amino acids of Artemis. Subsequent iterations with the PSI-BLAST program highlighted significant similarities of the first 150 amino acids to well-established members of the metallo-β-lactamase superfamily.

The metallo-β-lactamase fold, first described for the *Bacillus cereus* β-lactamase (Carfi et al., 1995), is adopted by various metallo-enzymes with a widespread distribution and substrate specificity (Aravind, 1997). It consists in a four-layered β-sandwich with two mixed β-sheets flanked by α-helices, with the metal-binding sites located at one edge of the β-sandwich. Sequence analysis as well as secondary structure prediction for Artemis clearly indicated the conservation of motifs typical of the metallo-β-lactamase fold. This is true in particular for the amino acids D17, [HXHKDH]33-38 (SEQ ID NO: 35), H115, and D136 participating in the metalbinding pocket and representing the catalytic site of the metallo-β- lactamases. The last metal-binding residue of the metallo-β-lactamases , H225 in *Tenotrophomonas maltophilia* metallo-β-lactamase (1SML), which is located at the end of a β-strand (strand β12) is absent in Artemis/SNM 1 /PSO2, but could be functionally substituted by the aspartic acid D165 of Artemis, also conserved in SNM1/PSO2. The later residue is located at the end of a predicted β-strand, separated by an α-helix from the strand bearing the preceding metal-binding residue.

Example 6

In Vitro Mutagenesis of Artemis Gene

The analysis of the Artemis protein sequence revealed revealed the existence of a putative metallo-β-beta lactamase domain (M1 to R179) which suggests that Artemis could have some catalytic function such as hydrolase. This domain is followed by another domain (E180 to S385) that was called β-CASP for β-Lactamase CPSF-Artemis-SNM1-PS02 associated domain. The β-CASP domain is always associated to the β-lact domain in a series of proteins with function on the metabolism of nucleic acids (DNA repair, RNA processing . . . ). Finally the last domain (C-ter) comprises E386 to T692. The role and the interdependence of these two domains was analyzed in vitro by generating mutants and testing their activity both on V(D)J recombination and DNA repair.

Results

V(D)J Recombination

The assay is based on the transfection of a fibroblast with Rag1 and Rag2 expression construct to analyze the V(D)J recombination of an extrachromosomal substrate (pHRec-CJ or pHRec-CS, see example 4). The βLact+βCASP region (M1 to S385) is sufficient to complement the V(D)J recombination defect in fibroblasts from Artemis deficient (RS-SCID) patients.

However, the βLact domain (M1 to R179) alone does not complement this defect. There is no activity either when using βCASP-Cter (E180 to T692) or C-ter (E386 to T692) configurations of Artemis.

The catalytic site of metallo-β-lactamases in bacteria is characterized by the arrangement of several conserved His and Asp residues which bind Zn atoms and confer the hydrolase activity. Many of these residues are also conserved in Artemis which further suggests the possible hydrolase activity of Artemis.

Several of these His and Asp residues were mutated to Val and the residual function of the protein was analyzed in the V(D)J assay.

D17A, H35A, D37A, and D136A almost completely abolished the function of Artemis while H165A and H319A reduced its activity. H38A and H151A seem to have no effect.

DNA Repair

This assay is based on the analysis of the sensitivity to γ rays of RS-SCID fibroblasts transduced with a retroviral vector expressing various form of Artemis. While βLact-βCASP/ C-ter complements the hyper radiosensitivity of RS-SCID cells, βLact-βCASP has no effect.

CONCLUSIONS

This mutagenesis experiments suggests that Artemis probably has some catalytic activity, as hypothesized by its homology with bacterial metallo-β-lactamases.

The βLact+βCASP domain of Artemis carries this catalytic activity since 1) it can ensure a V(D)J recombination on extrachromosomal substrates and 2) mutation of several putative catalytic residues (His and Asp) abolish the function.

Nevertheless, it is interesting to notice that the bLact+ bCASP domain does not seem to be not sufficient by itself to allow for Artemis activity in the context of the whole chromosome, as the full length Artemis protein, or at least part of the C-term domain, seems required to complement the radiosensitivity phenotype.

This suggests that Artemis probably interacts with other proteins in the context of its substrate within chromatin.

Based on this result, it is possible that the V(D)J recombination activity on endogenous (in chromatin vs. extrachromosomal) Ig and TCR genes may also require the entire Artemis protein.

This situation is somehow similar to that of the Rag2 protein. In Rag2, a core region is necessary and sufficient to drive recombination of extrachromosomal substrates while it is ineffective in the rearrangement of endogenous loci.

Example 7

Analysis of Patients with Partial Artemis Deficiency

Observation

In a survey of SCID patients, the inventors came across 4 cases (in 2 families) presenting a complex phenotype resembling Ataxia telangectasia, although without clear ataxia. These patients suffered from severe lymphopenia and hypogammaglobulinemia.

In some of these patients the finding of chromosomal aberrations on lymphocytes suggested that they might present a DNA-repair defect, which was further confirmed by showing hypersensitivity of Bone marrow to γ rays.

V(D)J recombination in fibroblasts of two of these patients (representing the two families) was either absent or severely diminished and was restored to normal level by addition of wt Artemis, as in example 4.

Lastly, it was possible to demonstrate that the Artemis gene was mutated in both cases, resulting in premature stop codons at T432 and D451 respectively (at the beginning of the C-Ter domain).

This observation somehow confirms the results of the in vitro mutagenesis (see example 6) showing that Artemis protein devoid of the complete C-Ter domain can still have recombination activity in the chromatin context in vivo (these patients do have some lymphocytes) but the efficiency on endogenous loci is very weak (these patients are strongly lymphopenic).

In two patients of the first family, the immune deficiency was accompanied by the development of very aggressive and disseminated lymphoproliferative syndrome (SLP) associated with the presence of EBV.

These SLPs can probably be assimilated to true B cell lymphomas based on their clonality and their aggressiveness.

CONCLUSION

The main conclusion of this observation is that Artemis can probably be considered as a "Caretaker" since its defect is apparently associated with the development of B cell lymphomas.

This idea is comforted by the literature that shows (in several reports) that defects in other factors of the V(D)J recombination/DNA repair (such as Ku80, DNA-PK, XRCC4, DNA-LigaseIV) in animal models always leads to the development of pro-B cell lymphomas when introduced on a P53−/− background, establishing them as true Caretakers.

This hypothesis can be experimented in an animal model.

REFERENCES

Aravind, L. (1997). An evolutionary classification of the matallo-β-lactamase fold. In Silico Biology.

Barnes et al. (1998). Targeted disruption of the gene encoding DNA ligase IV leads to lethality in embryonic mice. Curr-Biol 31, 1395-1398.

Biedermann et al. (1991). Scid mutation in mice confers hypersensitivity to ionizing radiation and a deficiency in DNA double-strand break repair. Proc. Natl. Acad. Sci. 88, 1394-1397.

Blunt et al. (1996). Identification of a nonsense mutation in the carboxyl-terminal region of DNA-dependant protein kinase catalytic subunit in the scid mouse. Proc. Natl. Acad. Sci. USA 93, 10285-10290.

Bosma et al. (1983). A severe combined immunodeficiency mutation in the mouse. Nature 301, 527-30.

Burge, C., and Karlin, S. (1997). Prediction of complete gene structures in human genomic DNA. J Mol Biol 268, 78-94.

Cameron et al. (1999). Crystal structure of human glyoxalase II and its complex with a glutathione thiolester substrate analogue. Structure Fold Des 7, 1067-78.

Carfi et al. (1995). The 3-D structure of a zinc metallo-beta-lactamase from *Bacillus cereus* reveals a new type of protein fold. Embo J 14, 4914-21.

Carney et al. (1998). The hMre11/hRad50 protein complex and Nijmegen breakage syndrome: linkage of double-strand break repair to the cellular DNA damage response. Cell 93, 477-86.

Cavazzana-Calvo et al. (1993). Increased radiosensitivity of granulocyte macrophage colony-forming units and skin fibroblasts in human autosomal recessive Severe Combined Immunodeficiency. J. Clin. Invest. 91, 1214-1218.

Chen et al. (2000). Response to RAG-mediated V(D)J cleavage by NBS1 and gamma-H2AX. Science 290, 1962-5.

Corneo et al. (2000). 3D clustering of human RAG2 gene mutations in Severe Combined Immune Deficiency (SCID). J. Biol. Chem. 275, 12672-12675.

Danska et al. (1996). Biochemical and genetic defects in the DNA-dependent protein kinase in murine scid lymphocytes. Mol Cell Biol 16, 5507-17.

Dronlcert et al. (2000). Disruption of mouse SNM1 causes increased sensitivity to the DNA interstrand cross-linking agent mitomycin C. Mol Cell Biol 20, 4553-61.

Eastman et al. (1996). Initiation of V(D)J recombination in vitro obeying the 12/23 rule. nature 380, 85-88.

Fischer et al. (1997). Naturally occurring primary deficiecies of the immune system. Annu. Rev. Immunol. 15, 93-124.

Frank et al. (I 1998). Late embryonic lethality and impaired V(D)J recombination in mice lacking DNA ligase IV. Nature 396, 173-7.

Fugmann et al. (2000). Identification of two catalytic residues in RAG1 that define a single active site within the RAG1/RAG2 protein complex. Mol Cell 5, 97-107.

Fulop, G. M., and Phillips, R. A. (1990). The scid mutation in mice causes a general defect in DNA repair. Nature 347, 479-482.

Gao et al. (1998). A targeted DNA-PKcs-null mutation reveals DNA-PK-independent functions for KU in V(D)J recombination. Immunity 9, 367-76.

Gao et al. (1998). A critical role for DNA end-joining proteins in both lymphogenesis and neurogenesis. Cell 95, 891-902.

Gottlieb, T. M., and Jackson, S. P. (1993). The DNA-dependant protein kinase: requirement for DNA ends and association with Ku antigen. Cell 72, 132-142.

Haber, J. E. (2000). Partners and pathways repairing a double-strand break. Trends Genet 16, 259-64.

Hendrickson et al. (1991). A link between double-strand break related repair and V(D)J recombination: the scid mutation. Proc. Natl. Acad. Sci. USA 88, 4061-4065.

Henriques, J. A., and Moustacchi, E. (1980). Isolation and characterization of pso mutants sensitive to photo-addition of psoralen derivatives in *Saccharomyces cerevisiae*. Genetics 95, 273-88.

Hu, D.C., Gahagan, S., Wara, D. W., Hayward, A., and Cowan, M. J. (1988). Congenital severe combined immunodeficiency disease (SCID) in American Indians. Pediatr. Res. 24, 239.

Jackson, S. P., and Jeggo, P. A. (1995). DNA double-strand break repair and V(D)J recombination: involvement of DNA-PK. Trends Biochem Sci 20, 412-5.

Jhappan, C., Morse, H. C. r., Fleischmann, R. D., Gottesman, M. M., and Merlino, G. (1997). DNA-PKcs: a T-cell tumour suppressor encoded at the mouse scid locus. Nat Genet 17, 483-6.

Junop, M. S., Modesti, M., Guarne, A., Ghirlando, R., Gellert, M., and Yang, W. (2000). Crystal structure of the xrcc4 DNA repair protein and implications for end joining. Embo J 19, 5962-70.

Kim, D. R., Dai, Y., Mundy, C. L., Yang, W., and Oettinger, M. A. (1999). Mutations of acidic residues in RAG1 define the active site of the V(D)J recombinase. Genes Dev 13, 3070-80.

Landree, M. A., Wibbenmeyer, J. A., and Roth, D. B. (1999). Mutational analysis of RAG1 and RAG2 identifies three catalytic amino acids in RAG1 critical for both cleavage steps of V(D)J recombination. Genes Dev 13, 3059-69.

Li, et al. (1998). The gene for severe combined immunodeficiency disease in Athabascan-speaking Native Americans is located on chromosome 10p. Am J Hum Genet 62, 136-44.

Li et al. (1995). The Xrcc4 Gene Encodes a Novel Protein Involved In Dna Double-Strand Break Repair and V(D)J Recombination. Cell 83, 1079-1089.

McBlane et al. (1995). Cleavage at a V(D)J recombination signal requires only RAG1 and RAG2 proteins and occurs in two steps. Cell 83, 387-95. Mombaerts et al. (1992). RAG-1 deficient mice have no mature B and T lymphocytes. Cell 68, 869-877.

Moshqus et al. (2000). A new gene involved in DNA double-strand break repair and V(D)J recombination is located on human chromosome 10p. Hum Mol Genet 9, 583-588.

Nicolas et al. (1996). Lack of detectable defect in DNA double-strand break repair and DNA-dependant protein kinase activity in radiosesitive human severe combined immunodeficiency fibroblasts. Eur. J. Immunol. 26, 1118-1122.

Nicolas et al. (1998). A human SCID condition with increased sensitivity to ionizing radiations and impaired V(D)J rearrangements defines a new DNA Recombination/Repair deficiency. J. Exp. Med 188, 627-634.

Nussenzweig et al. (1996). Requirement for Ku80 in growth and immunoglobulin V(D)J recombination. nature 382, 551-555.

Oettinger et al. (1990). RAG-1 and RAG-2, adjacent genes that synergistically activate V(D)J recombination. Science 248, 1517-1523.

Paull et al. (2000). A critical role for histone H2AX in recruitment of repair factors to nuclear foci after DNA damage. Curr Biol 10, 886-95.

Robins, P., and Lindahl, T. (1996). DNA ligase IV from HeLa cell nuclei. J Biol Chem 271, 24257-61.

Rogakou et al. (1999). Megabase chromatin domains involved in DNA double-strand breaks in vivo. J Cell Biol 146, 905-16.

Rogakou et al. (1998). DNA double-stranded breaks induce histone H2AX phosphorylation on serine 139. J Biol Chem 273, 5858-68.

Roth, D. B., and Craig, N. L. (1998). VDJ recombination: a transposase goes to work. Cell 94, 411-4.

Roth, D. B., and Gellert, M. (2000). New guardians of the genome. Nature 404, 823-5.

Roth et al. (1992). V(D)J recombination: Broken DNA molecules with covalently sealed (hairpin) coding ends in scid mouse thymocytes. Cell 70, 983-991.

Salamov, A. A., and Solovyev, V. V. (2000). Ab initio gene finding in *Drosophila* genomic DNA. Genome Res 10, 516-22.

Schatz et al. (1989). The V(D)J recombination activating gene, RAG-1. Cell 59, 1035-1048.

Schlissel et al. (1993). Double-strand signal sequence breaks in V(D)J recombination are blunt, 5'-phosphorylated, RAG-dependent, and cell cycle regulated. Genes Dev 7, 2520-32.

Schwarz et al. (1996). RAG mutations in human B cell-negative SCID. Science 274, 97-99.

Shin et al. (1997). A Kinase-Negative Mutation Of Dna-Pkcs In Equine Scid Results In Defective Coding and Signal Joint Formation. J. Immunol. 158, 3565-3569.

Shinkai et al. (1992). RAG-2 deficient mice lack mature lymphocytes owing to inability to initiate V(D)J rearrangement. Cell 68, 855-867.

Taccioli et al. (1998). Targeted disruption of the catalytic subunit of the DNA-PK gene in mice confers severe combined immunodeficiency and radiosensitivity. Immunity 9, 355-66.

Taccioli et al. (1993). Impairement of V(D)J recombination in double-strand break repair mutants. Science 260, 207-210.

The invention claimed is:

1. An isolated nucleic acid molecule selected from the group consisting of:
   a) SEQ ID NO:1, nucleotides 39-2114 of SEQ ID NO:1, or nucleotides 60-2114 of SEQ ID NO:1 and
   b) an isolated and purified nucleic acid comprising the nucleic acid of a).

2. A vector comprising the nucleic acid molecule of claim 1.

3. An isolated host cell comprising the vector of claim 2.

4. A process of producing a protein involved in V(D)J recombination and/or DNA repair comprising the steps of:
   a) expressing the nucleic acid molecule of claim 1 in a suitable host to synthesize a protein involved in V(D)J recombination and/or DNA repair and
   b) isolating the protein involved in V(D)J recombination and/or DNA repair.

5. An isolated nucleic acid molecule that is the complement of the isolated nucleic acid molecule of claim 1.

6. An isolated protein or peptide coded by the nucleic acid of claim 1.

7. A monoclonal or polyclonal antibody that specifically recognizes the protein or peptide of claim 6.

8. A pharmaceutical composition comprising a pharmaceutically acceptable excipient with at least one of the nucleic acid of claim 1 or 5.

9. The isolated nucleic acid molecule of claim 1, wherein said isolated nucleic acid molecule comprises nucleotides 39-1193 or nucleotides 60-1193 of SEQ ID NO: 1.

10. A pharmaceutical composition comprising a pharmaceutically acceptable excipient with at least one of the vector of claim 2, the host cell of claim 3, the protein of claim 6, the antibody of claim 7, or a combination thereof.

* * * * *